US009511232B2

(12) United States Patent
Biele et al.

(10) Patent No.: US 9,511,232 B2
(45) Date of Patent: *Dec. 6, 2016

(54) IMPLANTABLE PULSE GENERATOR THAT GENERATES SPINAL CORD STIMULATION SIGNALS FOR A HUMAN BODY

(71) Applicant: GLOBUS MEDICAL, INC., Audubon, PA (US)

(72) Inventors: Christopher Biele, King of Prussia, PA (US); Raghavendra Angara, Norristown, PA (US); Saif Khalil, Wayne, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,626

(22) Filed: Jul. 22, 2015

(65) Prior Publication Data

US 2016/0015981 A1 Jan. 21, 2016

Related U.S. Application Data

(63) Continuation-in-part of application No. 14/213,186, filed on Mar. 14, 2014.
(Continued)

(51) Int. Cl.
*A61N 1/36* (2006.01)
*A61N 1/02* (2006.01)
(Continued)

(52) U.S. Cl.
CPC .......... *A61N 1/36185* (2013.01); *A61N 1/025* (2013.01); *A61N 1/36125* (2013.01);
(Continued)

(58) Field of Classification Search
CPC .. A61N 1/36185; A61N 1/025; A61N 1/0551; A61N 1/3752; A61N 1/3787; A61N 1/36178; A61N 1/37229; A61N 1/37235; A61N 1/36125; A61N 1/37223; A61N 1/0553; A61N 1/36071
See application file for complete search history.

(56) References Cited

U.S. PATENT DOCUMENTS

2004/0260214 A1* 12/2004 Echt .................. A61H 23/0245
601/46
2010/0042187 A1* 2/2010 Werder .............. A61N 1/36185
607/74
(Continued)

*Primary Examiner* — Paula J Stice

(57) ABSTRACT

An implantable pulse generator (IPG) that generates spinal cord stimulation signals for a human body includes a timing generator and high frequency generator. The timing generator generates timing signals that represent stimulation signals for multiple channels. The high frequency generator determines whether to modulate the timing signals and modulates them at a burst frequency according to stored burst parameters if the decision is yes. The high frequency generator can also independently control the pulse frequency of each channel according to the stored parameters. As such, the IPG provides the ability to generate both the low frequency and high frequency stimulation signals at different frequencies in different channels according to user programming in order to provide maximum flexibility in treatment.

9 Claims, 18 Drawing Sheets

Related U.S. Application Data

(60) Provisional application No. 61/792,654, filed on Mar. 15, 2013.

(51) Int. Cl.
*A61N 1/372* (2006.01)
*A61N 1/375* (2006.01)
*A61N 1/378* (2006.01)
*A61N 1/05* (2006.01)

(52) U.S. Cl.
CPC ........ *A61N 1/0553* (2013.01); *A61N 1/36071* (2013.01); *A61N 1/36178* (2013.01); *A61N 1/3752* (2013.01); *A61N 1/3787* (2013.01); *A61N 1/37229* (2013.01); *A61N 1/37235* (2013.01)

(56) References Cited

U.S. PATENT DOCUMENTS

| | | | | |
|---|---|---|---|---|
| 2010/0274115 A1* | 10/2010 | Werder | ................ | A61B 5/0031 600/378 |
| 2011/0160810 A1* | 6/2011 | Griffith | ................ | A61N 1/0531 607/72 |

* cited by examiner

IMPLANTABLE PULSE GENERATOR THAT GENERATES SPINAL CORD STIMULATION SIGNALS FOR A HUMAN BODY

CROSS REFERENCE TO RELATED APPLICATIONS

The present application is a continuation-in-part of U.S. patent application Ser. No. 14/213,186, filed Mar. 14, 2014, which claims priority to U.S. Provisional Application Ser. No. 61/792,654, filed Mar. 15, 2013, and entitled "SPINAL CORD STIMULATOR SYSTEM," all of which are herein incorporated by reference in their entirety.

TECHNICAL FIELD

This disclosure relates to stimulators using electrical pulses in a medical context, and more particularly, applying electrical stimulation signals to the spinal cord to control pain.

BACKGROUND

A Spinal Cord Stimulator (SCS) is used to exert pulsed electrical signals to the spinal cord to control chronic pain. Spinal cord stimulation, in its simplest form, comprises stimulating electrodes implanted in the epidural space, an implantable pulse generator implanted in the lower abdominal area or gluteal region, conducting wires connecting the electrodes to the electrical pulse generator, an electrical pulse generator remote control, and an electrical pulse generator charger. Spinal cord stimulation has notable analgesic properties and, at the present, is used mostly in the treatment of failed back surgery syndrome, complex regional pain syndrome and refractory pain due to ischemia.

Electrotherapy of pain by neurostimulation began shortly after Melzack and Wall proposed the gate control theory in 1965. This theory proposed that nerves carrying painful peripheral stimuli and nerves carrying touch and vibratory sensation both terminate in the dorsal horn (the gate) of the spinal cord. It was hypothesized that input to the dorsal horn of the spinal cord could be manipulated to "close the gate" to the nerves. As an application of the gate control theory, Shealy et al. implanted the first spinal cord stimulator device directly on the dorsal column for the treatment of chronic pain in 1971.

Spinal cord stimulation does not eliminate pain. The electrical pulses from the stimulator override the pain messages so that the patient does not feel the pain intensely. In essence, the stimulator masks the pain. A trial implantation is performed before implanting the permanent stimulator. The physician first implants a trial stimulator through the skin (percutaneously) to perform stimulations as a trial run. Because a percutaneous trial stimulator tends to move from its original location, it is considered temporary. If the trial is successful, the physician can then implant a permanent stimulator. The permanent stimulator is implanted under the skin of the abdomen with the leads inserted under the skin and subcutaneously fed to and inserted into the spinal canal. This placement of the stimulator in the abdomen is a more stable, effective location. The leads, which consist of an array of electrodes, can be percutaneous type or paddle type. Percutaneous electrodes are easier to insert in comparison with paddle type, which are inserted via incision over spinal cord and laminectomy.

There are a number of problems that exist in currently available implantable pulse generators that limit the full benefits of dorsal column stimulation from an effectiveness and patient user friendly perspective.

One problem is that the circuits in the current generators consume too much power. This requires frequent recharging, making it very inconvenient for patients. Another problem is that the current generators are limited in concurrently generating different stimulation patterns to treat different parts of the body simultaneously. Accordingly, when patients have varying degrees of pain in different parts of the body, it is difficult, if not impossible, to affectively treat all area of pain.

Therefore, it would be desirable to provide a system and method for generating stimulation patterns which resolve the problems discussed above.

SUMMARY OF THE DISCLOSURE

According to one aspect of the present invention, there is provided an implantable pulse generator (IPG) that generates spinal cord stimulation signals for a human body has a programmable signal generator that can generate the signals based on stored signal parameters without any intervention from a processor that controls the overall operation of the IPG. While the signal generator is generating the signals the processor can be in a standby mode to substantially save battery power.

According to another aspect of the present invention, there is provided an implantable pulse generator (IPG) that generates spinal cord stimulation signals for a human body has control registers that store stimulation signal parameters for stimulation channels with each channel capable of being associated with at least two electrodes and representing a particular stimulation signal pattern for the associated electrodes. An arbitrator continuously receives timing signals representing the stimulation signal patterns and selects one channel among the many channels as an active treatment channel in order to avoid two channels from being activated at the same time. The arbitrator provides flexibility in programming different pulse parameters for multiple stimulation channels without the possibility of overloading the power supply that generates the stimulation signal patterns.

According to another aspect of the present invention, there is provided an implantable pulse generator (IPG) that generates spinal cord stimulation signals for a human body, which includes a timing generator and high frequency generator. The timing generator generates timing signals that represent stimulation signals for multiple channels. The high frequency generator determines whether to modulate the timing signals and modulates them at a burst frequency according to stored burst parameters if the decision is yes. As such, the IPG provides the ability to generate both the low frequency and high frequency stimulation signals in different channels according to user programming.

According to another aspect of the present invention, there is provided an implantable pulse generator (IPG) that generates spinal cord stimulation signals for a human body, which includes a timing generator and high frequency generator. The timing generator generates timing signals that represent stimulation signals for multiple channels. The high frequency generator determines whether to modulate the timing signals and modulates them at a burst frequency according to stored burst parameters if the decision is yes. The high frequency generator can also independently control the pulse frequency of each channel according to the stored parameters. As such, the IPG provides the ability to generate both the low frequency and high frequency stimulation signals at different frequencies in different channels according to user programming in order to provide maximum flexibility in treatment.

According to another aspect of the present invention, there is provided an implantable pulse generator (IPG) that generates spinal cord stimulation signals for a human body, which includes an electrode driver for each electrode, which adjusts the amplitude of the timing signals and output an output current corresponding to the adjusted signals for transmission to the associated electrode so as to enable independent amplitude control of the stimulation signals for each stimulation pattern channel.

DETAILED DESCRIPTION

Implantable Pulse Generator (IPG)

Figure 1:
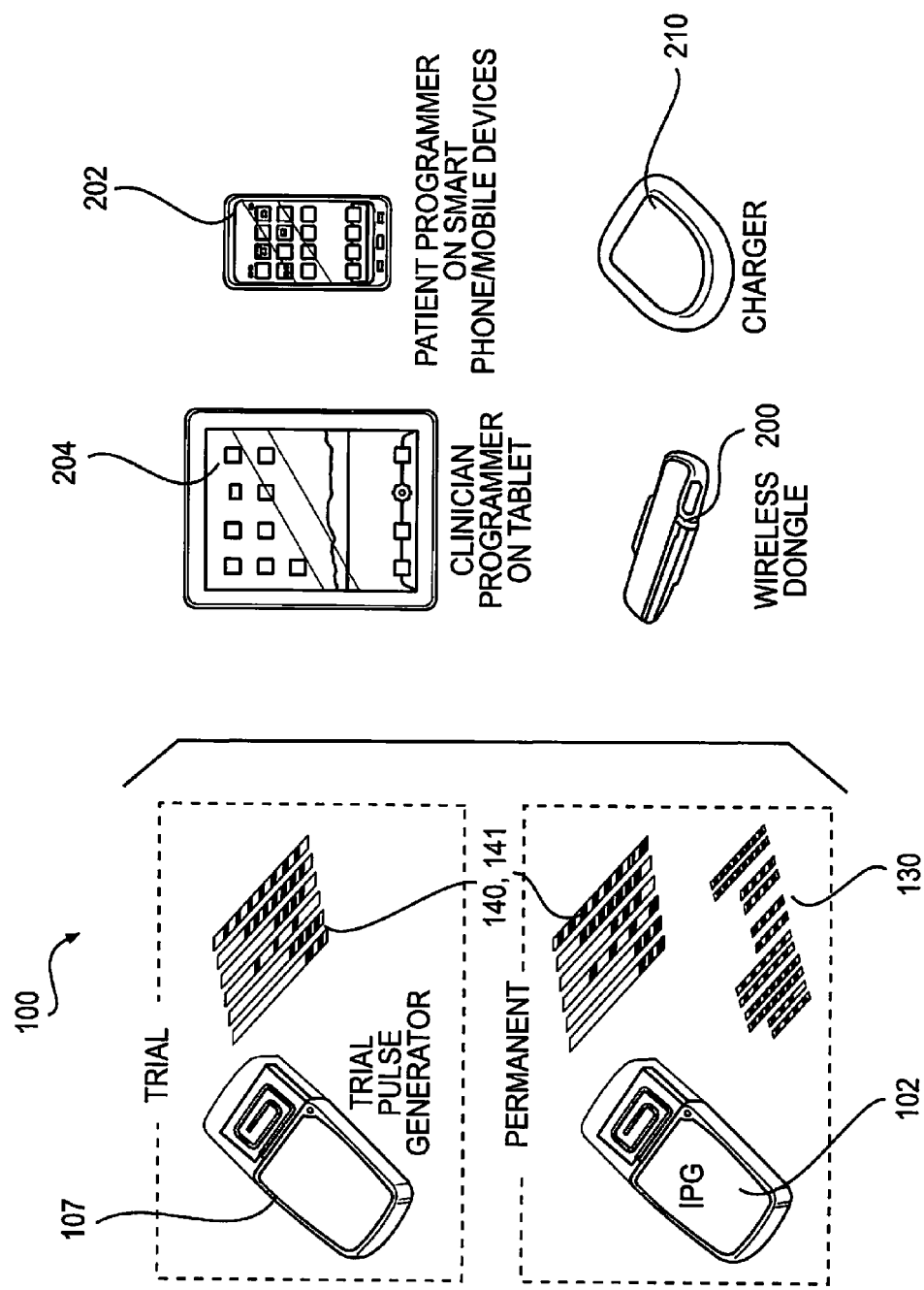
FIG. 1 depicts various components that can be included in a spinal cord stimulation system, according to an embodiment, during trial and permanent implantation.

FIG. 1 illustrates various components that can be included in a SCS system for the trial and the permanent installation periods. The spinal cord stimulator (SCS) 100 is an implantable device used to deliver electrical pulse therapy to the spinal cord in order to treat chronic pain. The implantable components of the system consist of an Implantable Pulse Generator (IPG) 102 and a multitude of stimulation electrodes 130. The IPG 102 is implanted subcutaneously, no more than 30 mm deep in an area that is comfortable for the patient while the stimulation electrodes 130 are implanted directly in the epidural space. The electrodes 130 are wired to the IPG 102 via leads 140, 141 which keep the stimulation pulses isolated from each other in order to deliver the correct therapy to each individual electrode 130.

The therapy delivered consists of electrical pulses with controlled current amplitude ranging from +12.7 to −12.7 mA (current range 0-25.4 mA). These pulses can be programmed in both length and frequency from 10 μS to 2000 μS and 0.5 Hz to 1200 Hz. At any given moment, the sum of the currents sourced from the anodic electrodes 130 must equal the sum of the currents sunk by the cathodic electrodes 130. In addition, each individual pulse is bi-phasic, meaning that once the initial pulse finishes another pulse of opposite amplitude is generated after a set holdoff period. The electrodes 130 may be grouped into stimulation sets in order to deliver the pulses over a wider area or to target specific areas, but the sum of the currents being sourced at any one given time may not exceed 20 mA. A user can also program different stimulation sets (up to eight) with different parameters in order to target different areas with different therapies.

Figure 2:
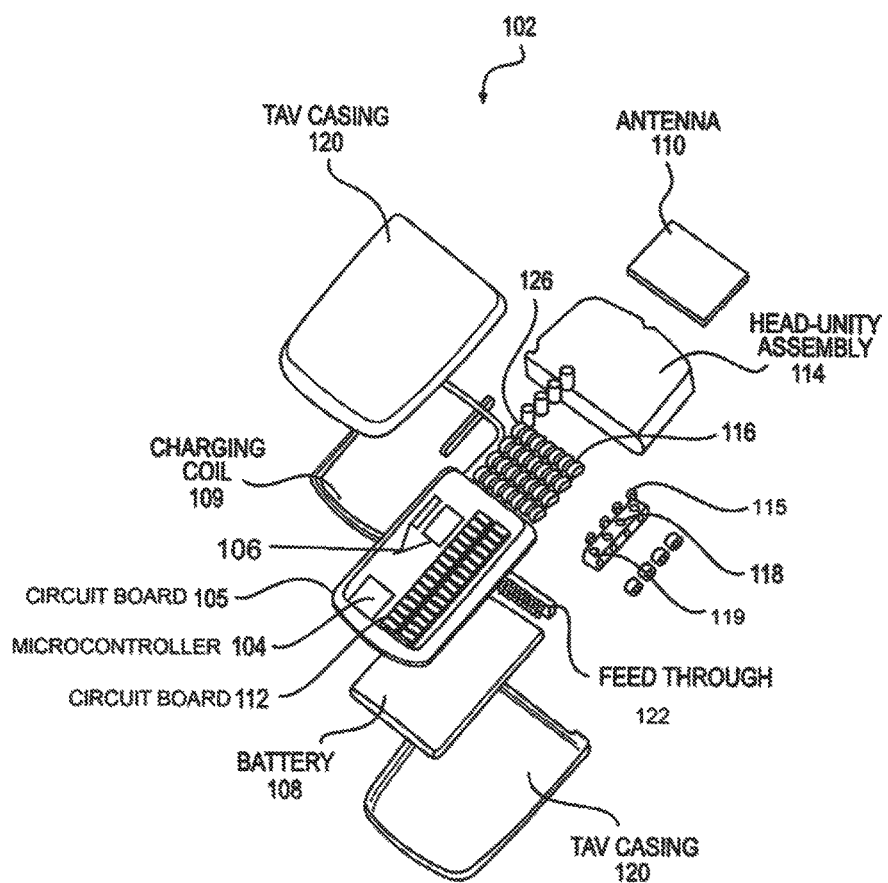
FIG. 2 depicts an exploded view of an implantable pulse generator (IPG) assembly, according to an embodiment.

FIG. 2 depicts an exploded view of an IPG 102. The IPG 102 consists of two major active components: microcontroller 104, ASIC 106, a battery 108, antenna 110, some support circuitry, and a multitude of output capacitors 112. The first of the major active components is the microcontroller 104 (which can also be referred to as microcontroller transceiver 104). It is responsible for receiving, decoding, and execution both commands and requests from the external remote. If necessary it passes these commands or requests onto the second major component, the ASIC 106. The ASIC 106 receives the digital data from the microcontroller 104 and performs the entire signal processing to generate the signals necessary for stimulation. These signals are then passed onto the stimulation electrodes 130 in the epidural space.

The ASIC 106 is comprised of a digital section and an analog section. The digital section is divided into multiple sections including; Timing Generators, Arbitration Control, Pulse Burst Conditioner, and Electrode Logic. The analog section receives the incoming pulses from the digital section and amplifies them in order to deliver the correct therapy. There are also a multitude of digital register memory elements that each section utilizes, both digital and analog.

The digital elements in the ASIC 106 are all made up of standard subsets of digital logic including logic gates, timers, counters, registers, comparators, flip-flips, and decoders. These elements are ideal for processing the stimulation pulses as all of them can function extremely fast—orders of magnitudes faster than the required pulse width. The elements all function at one single voltage, usually 5.0, 3.3, 2.5, or 1.8 volts.

The timing generators are the base of each of the stimulation sets. It generates the actual rising and falling edge triggers for each phase of the bi-phasic pulse. It accomplishes this by taking the incoming clock that is fed from the microcontroller 104 and feeding it into a counter. For the purpose of this discussion, assume the counter simply counts these rising clock edges infinitely. The output of the counter is fed into six different comparators. The comparators other input is connected to specific registers that are programmed by the microcontroller 104. When the count equals the value stored in the register, the comparator asserts a positive signal.

The first comparator is connected to the SET signal of a SR flip flop. The SR flip flop stays positive until the RESET signal is asserted, which the second comparator is connected to. The output of the SR flip flop is the first phase of the bi-phasic pulse. Its rising & falling edges are values stored in the registers and programmed by the microcontroller 104. The third and fourth comparators & registers work in exactly the same way to produce the second phase of the bi-phasic pulse using the second SR flip flop.

The fifth comparator is connected the RESET of the final SR-Flip flop in the timing generator. This flip flop is SET by the first comparator, which is the rising edge of the first pulse. The RESET is then triggered by the value the microprocessor programmed into the register connected to the comparator. This allows for a 'holdoff' period after the falling edge of the second pulse. The output of this third SR flip flop can be thought of as an envelope of the biphasic pulses indicating when this particular timing generator is active.

The final comparator of the system is once again connected to a register that stores the frequency values from the microprocessor. Essentially when the count reaches this value it triggers the comparator which is fed back to the counter to reset it to zero and beginning the entire pulse generation cycle again. The ASIC 106 may contain many of these timing generators as each can control anywhere from two to all of the electrodes 130 connected to the IPG 102 at a time. However, when there is more than one timing generator and multiple channels have been actively programmed then there needs to be a mechanism for suppressing a second channel from turning on when another is already active.

The next circuit block contained in the IPG 102 is the arbitrator. The arbitrator functions by looking at each of the timing generators' envelope signals and makes sure only one can be active at a time. If a second tries to activate then the arbitrator suppresses that signal.

The arbitrator accomplishes this by bringing each of the channel envelope signals into a rising edge detection circuit. Once one is triggered it is fed into the SET pin of an SR flip flop. The output of this SR-flip flop is fed into all of the other rising edge detectors in order to suppress them from triggering. The channel envelope signal is also fed into a falling-edge detector which is then fed into the RESET of the same SR flip flop. The output of the SR flip flops are then connected to switches whose outputs are all tied together that turn on/off that channels particular biphasic pulse train. Therefore, the output of this circuit element is a single bi-phasic pulse train and a signal designating which timing generator that particular pulse train is sourced from. Essentially, the circuit looks for a channel to go active. Once it finds one it suppresses all others until that channel becomes inactive.

The next section of the circuit works very similarly to the timing generators to create a high speed burst pulse train that is then combined with the stimulation pulse train to create a bursted bi-phasic pulse train if desired.

It accomplishes this by taking the incoming clock that is fed from the microcontroller 104 and feeding it into a counter. The counter can count these rising clock edges infinitely. The counter is only active during a single phase of the bi-phasic signal and begins counting as soon as the rising edge is detected. The output of the counter is fed into a comparator, along with a microcontroller-programmed register, whose output is connected to the reset pin on the counter. Therefore, this counter will simply count to a programmed value and reset. This programmed value is the burst frequency.

The output of the comparator is then fed into an edge detection circuit and then a flip flop that combines it with the actual stimulation pulse train to create a single phase bursted stimulation pulse. The entire circuit is duplicated for the second phase of the signal resulting in the desired bursted bi-phasic pulse train. The stimulation signal is now handed over to the electrode logic stage.

The electrode logic conditions and directs the bi-phasic signals to the analog section of the ASIC 106. At this point, the bi-phasic signals contain all of the pertinent timing information, but none of the required amplitude information. The incoming signals include the bi-phasic pulse train and another signal designating which timing generator the current active train came from. Each electrode logic cell has a register for each timing generator that stores this particular electrode's 130 amplitude values for that timing generator. The electrode logic cell uses the designation signal to determine which register to pull the amplitude values from, e.g. if the third timing generator is passed through the arbitration circuit then the electrode logic would read the value from the third register.

Once the value is pulled from the register, it goes through a series of logic gates. The gates first determine that the electrode 130 should be active. If not, no further action is taken and the analog section of the electrode output is not activated, thereby saving precious battery 108 power. Next, a determination is made if the particular electrode 130 is an anode or cathode. If the electrode is deemed to be an anode, the electrode logic passes the amplitude information and the biphasic signal to the positive current (digital to analog converter) DAC in the analog section of the ASIC 106. If the electrode is deemed to be a cathode, the electrode logic passes the amplitude information and the biphasic signal to the negative current DAC in the analog section of the ASIC 106. The electrode logic circuit must make these decisions for each phase of the bi-phasic signal as every electrode 130 will switch between being an anode and a cathode.

The analog elements in the ASIC 106 are uniquely designed in order to produce the desired signals. The basis of analog IC design is the field effect transistor (FET) and the type of high current multiple output design required in SCS 100 means that the bulk of the silicon in the ASIC 106 will be dedicated to the analog section.

The signals from the electrode output are fed into each current DAC when that specific electrode 130 should be activated. Each electrode 130 has a positive and a negative current DAC, triggered by the electrode logic and both are never active at the same time. The job of each current DAC is, when activated, to take the digital value representing a stimulation current amplitude and produce an analog representation of this value to be fed into the output stage. This circuit forms half of the barrier between the digital and analog sections of the ASIC 106.

The digital section of the ASIC 106 is built upon a technology that only allows small voltages to exist. In moving to the analog section, the output of the current DAC (which is a low level analog signal) must be amplified to a higher voltage for use in the analog section. The circuit that performs this task is called a power level shifter. Because this circuit is built upon two different manufacturing technologies and requires high precision analog circuits built upon a digital base, it can be difficult to implement.

Once the voltages have been converted for usage in the analog portion of the ASIC 106 the voltages are passed on to the output current stages. There are two current sources per electrode output. One will source a positive current and one will sink a negative current, but both will never be active simultaneously. The current sources themselves are made up of analog elements similar to a Howland current source. There is an input stage, and an amplification stage with feedback through a sensing component to maintain the constant current. The input stage takes the analog voltage values from the power level shifter and produces an output pulse designated for the amplifier. The amplifier then creates the pulses of varying voltages but constant current flow. The sources are capable of sourcing or sinking up to 12.7 mA at 0.1 mA resolution into a load of up to 1.2 k Ohms. This translates into range of 15 volts, which will vary depending on the load in order to keep the current constant.

The microcontroller 104 to ASIC 106 interface is designed to be as simple as possible with minimal bus 'chatter' in order to save battery 108 life. The ASIC 106 can be a collection of registers programmed via a standard I²C or SPI bus. Since the ASIC 106 is handling all the power management, there will also be a power good (PG) line between the two chips 104, 106 in order to let the microcontroller 104 know when it is safe to power up. The ASIC 106 will also need to use a pin on the microcontroller 104 in order to generate a hardware interrupt in case anything goes awry in the ASIC 106. The final connection is the time base for all of the stimulation circuitry. The ASIC 106 will require two clocks, one for its internal digital circuitry which will be fed directly from the microcontroller 104 clock output, and one to base all stimulation off of which will need to be synthesized by the microcontroller 104 and fed to the ASIC 106. All commands and requests to the ASIC 106 will be made over the I²C or SPI bus and will involve simply reading a register address or writing to a register. Even when the ASIC 106 generates a hardware interrupt, it will be the responsibility of the microcontroller 104 to poll the ASIC 106 and determine the cause of the interrupt.

The wireless interface is based upon the FCCs MedRadio standard operating in the 402-405 MHz range utilizing up to 10 channels for telemetry. The protocol implemented is chosen to minimize transmission and maximize battery 108 life. All processing will take place on the user remote/programmer and the only data transmitted is exactly what will be used in the microcontroller 104 to ASIC 106 bus. That is, all of the wireless packets will contain necessary overhead information along with only a register address, data to store in the register, and a command byte instructing the microcontroller 104 what to do with the data. The overhead section of the wireless protocol will contain synchronization bits, start bytes, an address which is synchronized with the IPG's 102 serial number, and a CRC byte to assure proper transmission. The packet length is kept as small as possible in order to maintain battery 108 life. Since the IPG 102 cannot listen for packets all the time due to battery 108 life, it cycles on for a duty cycle of less than 0.05% of the time. This time value can be kept small as long as the data packets are also small. The user commands needed to run the system are executed by the entire system using flows.

The IPG 102 uses an implantable grade Li ion battery 108 with 215 mAHr with zero volt technology. The voltage of the battery 108 at full capacity is 4.1 V and it supplies current only until it is drained up to 3.3 V which is considered as 100% discharged. The remaining capacity of the battery 108 can be estimated at any time by measuring the voltage across the terminals. The maximum charge rate is 107.5 mA. A Constant Current, Constant Voltage (CCCV) type of regulation can be applied for faster charging of the battery 108.

The charging coil 109 is made up of 30 turns of 30 AWG copper magnet wires. The ID, OD, and the thickness of the coil are 30, 32, and 2 mm, respectively. Inductance L2 is measured to be 58 uH, a 80 nF capacitor is connected to it to make a series resonance tank at 74 kHz frequency. In the art of induction charging, two types of rectifiers are considered to convert the induced AC into usable DC, either a bridge full wave rectifier or a voltage doubler full wave rectifier. To obtain a higher voltage, the voltage double full wave rectifier is used in this application. The rectifier is built with high speed Schottky diodes to improve its function at high frequencies of the order 100 kHz. A Zener diode and also a 5V voltage regulator are used for regulation. This circuit will be able to induce AC voltage, rectify to DC, regulate to 5V and supply 100 mA current to power management IC that charges the internal battery 108 by CCCV regulation.

The regulated 5V 100 mA output from the resonance tank is fed to, for example, a Power Management Integrated Circuit (PMIC) MCP73843. This particular chip was specially designed by Microchip to charge a Li ion battery 108 to 4.1 V by CCCV regulation. The fast charge current can be regulated by changing a resistor; it is set to threshold current of 96 mA in the example circuit. The chip charges the battery 108 to 4.1V as long as the current received is more than 96 mA. However, if the supply current drops below 96 mA, it stops to charge the battery 108 until the supply is higher than 96 again. For various practical reasons, if the distance between the coils increases, the coil 109 receives lesser current than the regulated value, and instead of charging the battery 108 slowly, it pauses the charging completely until it receives more than 96 mA. It is understood to those with skill in the art that other power management chips can be used and the power management chip is not limited to the PMIC MCP738432 chip.

All the functions of the IPG 102 are controlled from outside using a hand held remote controller specially designed for this device. Along with the remote control, an additional control is desirable to operate the IPG 102 if the remote control was lost or damaged. For this purpose a Hall effect based magnet switch was incorporated to either turn ON or turn OFF the IPG 102 using an external piece of magnet. Magnet switch acts as a master control for the IPG 102 to turn on or off. A south pole of sufficient strength turns the output on and a north pole of sufficient strength turns the output off. The output is latched so that the switch continues to hold the state even after the magnet is removed from its vicinity.

The IPG 102 is an active medical implant that generates an electrical signal that stimulates the spinal cord. The signal is carried through a stimulation lead 140 that plugs directly into the IPG 102. The IPG 102 recharges wirelessly through coil 109, and communicates via RF radio antenna 110 to change stimulation parameters. The IPG 102 is implanted up to 3 cm below the surface of the skin and can be fixed to the fascia by passing two sutures through holes in the epoxy header 114. The leads 140 are electrically connected to the IPG 102 through a lead contact system 116, a cylindrical spring-based contact system with inter-contact silicone seals. The leads 140 are secured to the IPG 102 with a set screw 119 that actuates within locking housing 118. Set screw compression on the lead's 140 fixation contact can be governed by a disposable torque wrench. The wireless recharging is achieved by aligning the exterior induction coil on the charger with the coil 109 within the IPG 102. The RF antenna within the remote's dongle 200 communicates with the RF antenna 110 in the IPG's 102 epoxy header 114. FIG. 2 illustrates an exploded view of the IPG 102 assembly.

Figure 3:
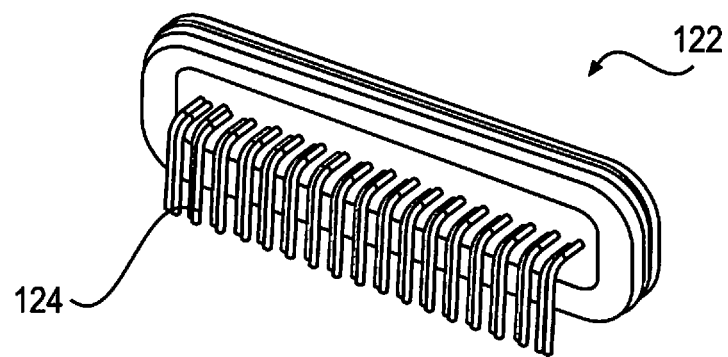
FIG. 3 depicts a feedthrough assembly of an implantable pulse generator (IPG) assembly, according to an embodiment.
Figure 6:
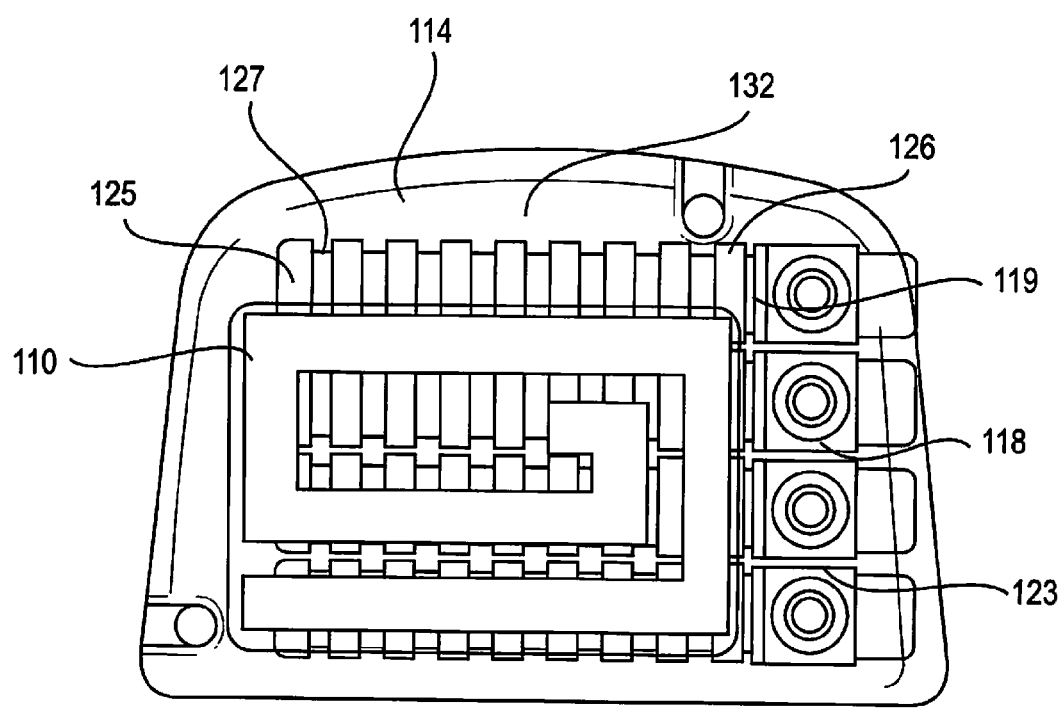
FIG. 6 depicts a head unit assembly of an implantable pulse generator (IPG) assembly, according to an embodiment.
Figure 7:
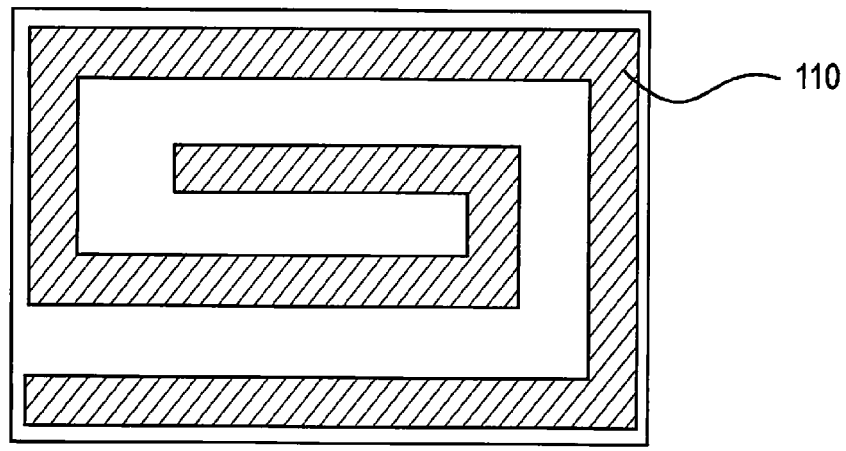
FIG. 7 depicts an RF antenna of an implantable pulse generator (IPG) assembly, according to an embodiment.

The IPG 102 is an assembly of a hermetic titanium (6Al-4V) casing 120 which houses the battery 108, microcontroller 104, ASIC 106, and coil 109. The IPG 102 further includes an epoxy header 114 (see FIG. 6), which houses the lead contact assembly 116, locking housing 118, and RF antenna 110 (see FIGS. 6 and 7). The internal electronics are connected to the components within the epoxy head through a hermetic feedthrough 122, as shown in FIG. 3. The feedthrough 122 is a titanium (6Al-4V) flange with an alumina window and gold trimming. Within the alumina window are thirty-four platinum-iridium (90-10) pins that interface internally with a direct solder to the circuit board, and externally with a series of platinum iridium wires laser-welded to the antenna 110 and lead contacts 126. The IPG 102 interfaces with 32 electrical contacts 126, which are arranged in four rows of eight contacts 126. Thirty two of the feedthrough's 122 pins 124 interface with the contacts 126, while two interface with the antenna 110, one to the ground plane and one to the antenna 110 feed.

Figure 4:
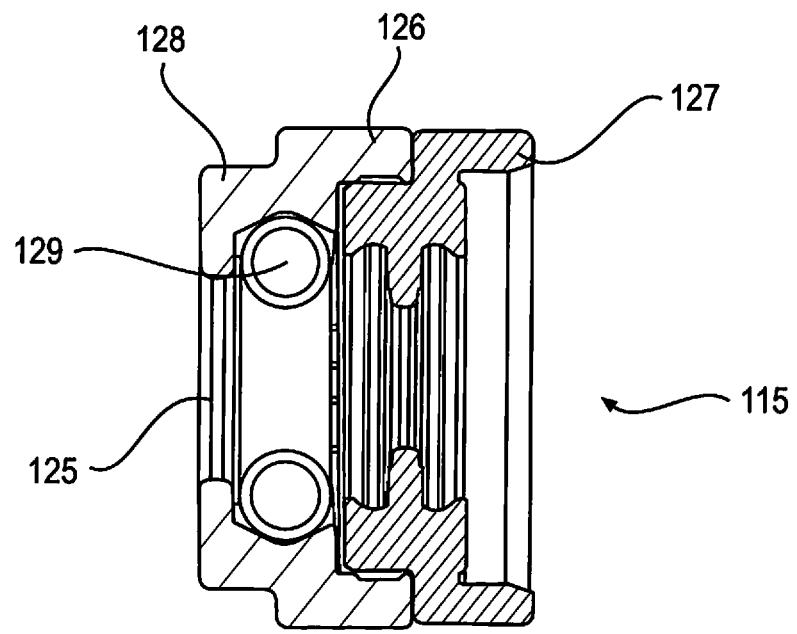
FIG. 4 depicts a lead contact system of an implantable pulse generator (IPG) assembly, according to an embodiment.
Figure 5:
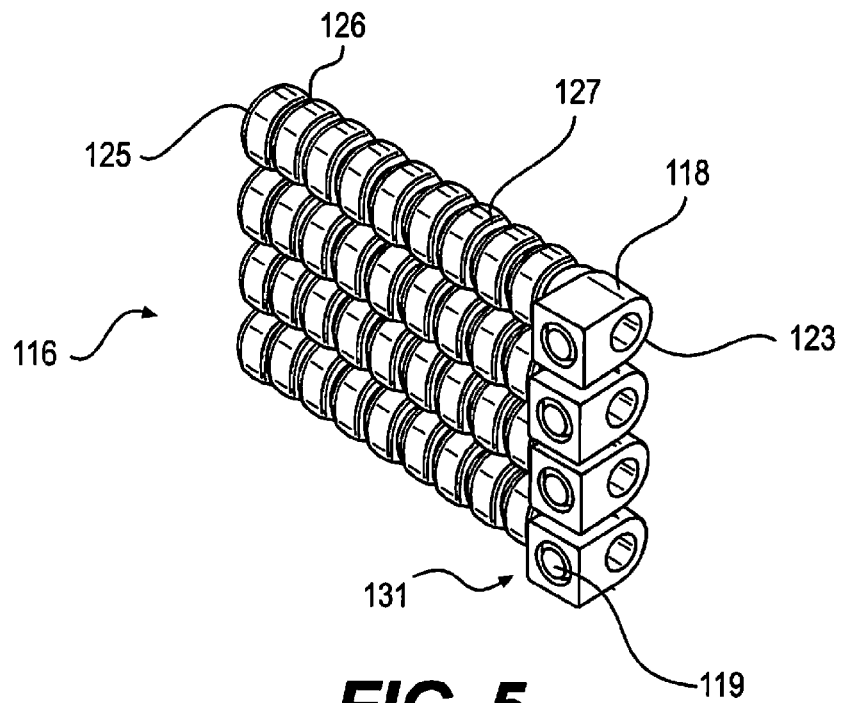
FIG. 5 depicts a lead contact assembly of an implantable pulse generator (IPG) assembly, according to an embodiment.

FIGS. 4 and 5 depict a lead contact system 115 and assembly 116, respectively. The lead contacts 126 consist of an MP35N housing 128 with a platinum-iridium 90-10 spring 129. Each contact 126 is separated by a silicone seal 127. At the proximal end of each stack of 8 contacts 126 is a titanium (6Al-4V) cap 125 which acts as a stop for the lead 140. At the distal end is a titanium (6Al-4V) set screw 119 and block 118 for lead fixation. At the lead entrance point is a silicone tube 123 which provides strain relief as the lead 140 exits the head unit 114, and above the set screw 119 another silicone tube 131 with a small internal canal allows the torque wrench to enter but does not allow the set screw 119 to back out. In addition to the contacts 126 and antenna 110, the header 114 also contains a radiopaque titanium (6Al-4V) tag 132 which allows for identification of the device under fluoroscopy. The overmold of the header 114 is Epotek 301, a two-part, biocompatible epoxy. FIGS. 4, 5, 6, and 7 depict illustrations of lead contact system 115, lead contact assembly 116, head unit assembly 114, and RF antenna 110, respectively.

Internal to the titanium (6Al-4V) case 120 are the circuit board 105, battery 108, charging coil 109, and internal plastic support frame. The circuit board 105 can be a multi-layered FR-4 board with copper traces and solder mask coating. Non-solder masked areas of the board can be electroless nickel immersion gold. The implantable battery 108, all surface mount components, ASIC 106, microcontroller 104, charging coil 109, and feedthrough 122 will be soldered to the circuit board 105. The plastic frame, made of either polycarbonate or ABS, will maintain the battery's 108 position and provide a snug fit between the circuitry 105 and case 120 to prevent movement. The charging coil 109 is a wound coated copper.

Leads

Figure 8:
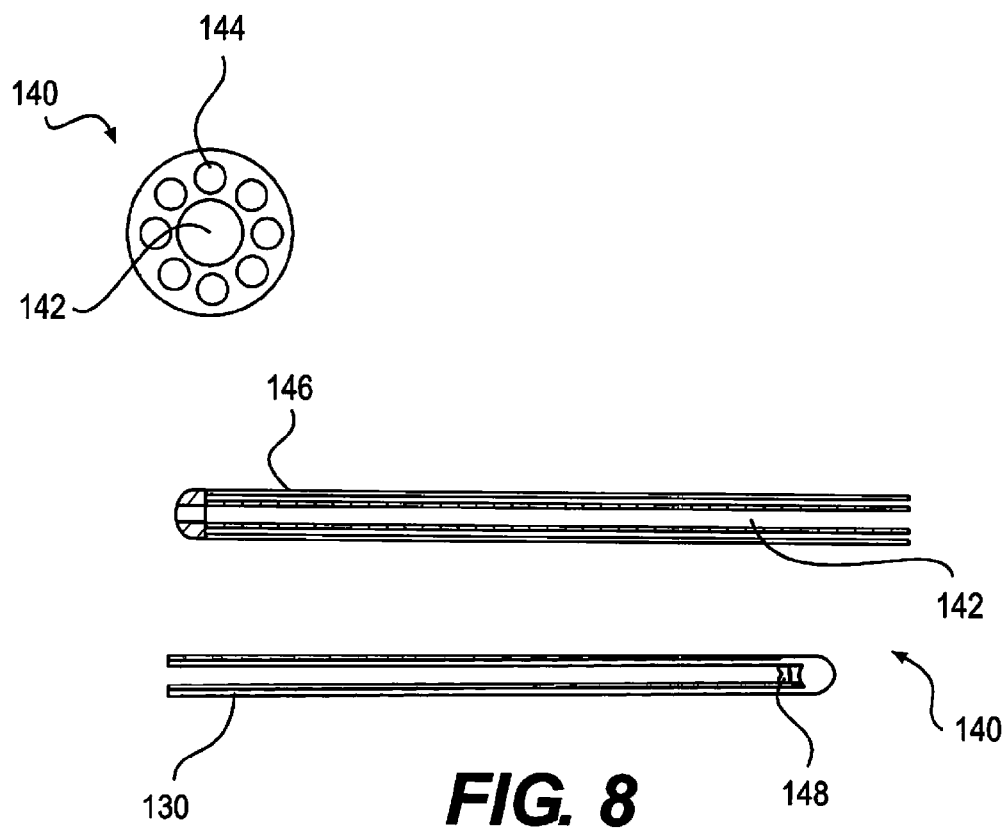
FIG. 8 depicts a percutaneous lead, according to an embodiment.

The percutaneous stimulation leads 140, as depicted in FIG. 8, are a fully implantable electrical medical accessory to be used in conjunction with the implantable SCS 100. The primary function of the lead is to carry electrical signals from the IPG 102 to the target stimulation area on the spinal cord. Percutaneous stimulation leads 140 provide circumferential stimulation. The percutaneous stimulation leads 140 provide a robust, flexible, and bio-compatible electric connection between the IPG 102 and stimulation area. The leads 140 are surgically implanted through a spinal needle, or epidural needle, and are driven through the spinal canal using a steering stylet that passes through the center of the lead 140. The leads 140 are secured mechanically to the patient using either an anchor or a suture passed through tissue and tied around the body of the lead 140. The leads 140 are secured at the proximal end with a set-screw 119 on the IPG 102 which applies radial pressure to a blank contact on the distal end of the proximal contacts.

The percutaneous stimulation leads 140 consist of a combination of implantable materials. Stimulation electrodes 130 at the distal end and electrical contacts at the proximal end are made of a 90-10 platinum-iridium alloy. This alloy is utilized for its bio-compatibility and electrical conductivity. The electrodes 130 are geometrically cylindrical. The polymeric body of the lead 140 is polyurethane, chosen for its bio-compatibility, flexibility, and high lubricity to decrease friction while being passed through tissue. The polyurethane tubing has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. The wires 146 are laser welded to the contacts and electrodes 130, creating an electrical connection between respective contacts on the proximal and distal ends. The leads 140 employ a platinum-iridium plug 148, molded into the distal tip of the center lumen 142 to prevent the tip of the steering stylet from puncturing the distal tip of the lead 140. Leads 140 are available in a variety of 4 and 8 electrode 130 configurations. These leads 140 have 4 and 8 proximal contacts (+1 fixation contact), respectively. Configurations vary by electrode 130 number, electrode 130 spacing, electrode 130 length, and overall lead 140 length.

Figure 9:
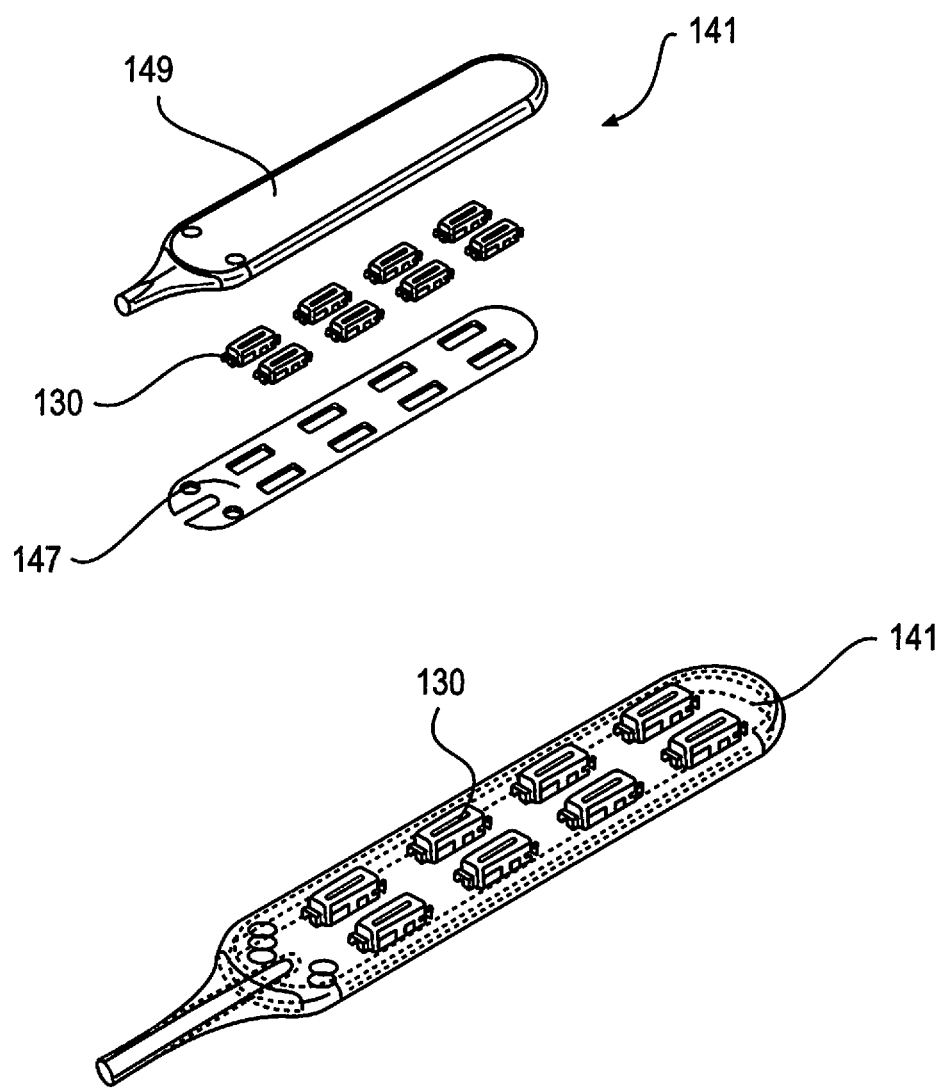
FIG. 9 depicts a paddle lead, according to an embodiment.

The paddle stimulation leads 141, as depicted in FIG. 9, are a fully implantable electrical medical accessory to be used in conjunction with the implantable SCS 100. The primary function of the paddle lead 141 is to carry electrical signals from the IPG 102 to the target stimulation area on the spinal cord. The paddle leads 141 provide uni-direction stimulation across a 2-dimensional array of electrodes 130, allowing for greater precision in targeting stimulation zones. The paddle stimulation leads 141 provide a robust, flexible, and bio-compatible electric connection between the IPG 102 and stimulation area. The leads 141 are surgically implanted through a small incision, usually in conjunction with a laminotomy or laminectomy, and are positioned using forceps or a similar surgical tool. The leads 141 are secured mechanically to the patient using either an anchor or a suture passed through tissue and tied around the body of the lead 141. The leads 141 are secured at the proximal end with a set-screw on the IPG 102 which applies radial pressure to a fixation contact on the distal end of the proximal contacts.

The paddle stimulation leads 141 consist of a combination of implantable materials. Stimulation electrodes 130 at the distal end and electrical contacts at the proximal end are made of a 90-10 platinum-iridium alloy utilized for its bio-compatibility and electrical conductivity. The polymeric body of the lead 141 is polyurethane, chosen for its bio-compatibility, flexibility, and high lubricity to decrease friction while being passed through tissue. The polyurethane tubing has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. At the distal tip of the paddle leads 141 is a 2-dimensional array of flat rectangular electrodes 130 molded into a flat silicone body 149. In an embodiment, one side of the rectangular electrodes 130 is exposed, providing uni-directional stimulation. The wires 146 are laser welded to the contacts and electrodes 130, creating an electrical connection between respective contacts on the proximal and distal ends. Also molded into the distal silicone paddle is a polyester mesh 147 adding stability to the molded body 149 while improving aesthetics by covering wire 146 routing. The number of individual 8-contact leads 141 used for each paddle 141 is governed by the number of electrodes 130. Electrodes 130 per paddle 141 range from 8 to 32, split into between one and four proximal lead 141 ends. Each proximal lead 141 has 8 contacts (+1 fixation contact). Configurations vary by electrode 130 number, electrode 130 spacing, electrode length, and overall lead length.

Figure 10:
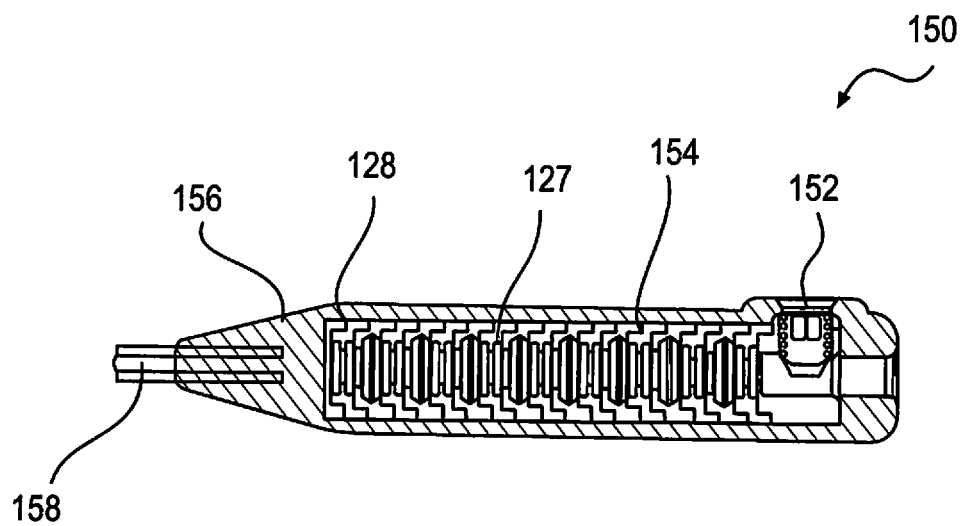
FIG. 10 depicts a lead extension, according to an embodiment.

The lead extensions 150, as depicted in FIG. 10, are a fully implantable electrical medical accessory to be used in conjunction with the implantable SCS 100 and either percutaneous 140 or paddle 141 leads. The primary function of the lead extension 150 is to increase the overall length of the lead 140, 141 by carrying electrical signals from the IPG 102 to the proximal end of the stimulation lead 140, 141. This extends the overall range of the lead 140, 141 in cases where the length of the provided leads 140, 141 are insufficient. The lead extensions 150 provide a robust, flexible, and bio-compatible electric connection between the IPG 102 and proximal end of the stimulation lead 140, 141. The extensions 150 may be secured mechanically to the patient using either an anchor or a suture passed through tissue and tied around the body of the extension 150. Extensions 150 are secured at the proximal end with a set-screw 119 on the IPG 102 which applies radial pressure to a fixation contact on the distal end of the proximal contacts of the extension 150. The stimulation lead 140, 141 is secured to the extension 150 in a similar fashion, using a set screw 152 inside the molded tip of extension 150 to apply a radial pressure to the fixation contact at the proximal end of the stimulation lead 140, 141.

The lead extension 150 consists of a combination of implantable materials. At the distal tip of the extension 150 is a 1×8 array of implantable electrical contacts 154, each consisting of MP35 housing 128 and 90-10 platinum-iridium spring. A silicone seal 127 separates each of the housings 128. At the proximal end of the contacts is a titanium (6Al4V) cap which acts as a stop for the lead, and at the distal tip, a titanium (6Al4V) block and set screw 152 for lead fixation. The electrical contacts at the proximal end are made of a 90-10 platinum-iridium alloy utilized for its bio-compatibility and electrical conductivity. The polymeric body 156 of the lead 150 is polyurethane, chosen for its bio-compatibility, flexibility, and high lubricity to decrease friction while being passed through tissue. The polyurethane tubing 158 has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes. These wires 146 are a bundle of MP35N strands with a 28% silver core. The wires 146 are individually coated with ethylene tetrafluoroethylene (ETFE), to provide an additional non-conductive barrier. Each lead extension 150 has 8 proximal cylindrical contacts (+1 fixation contact).

Figure 11:
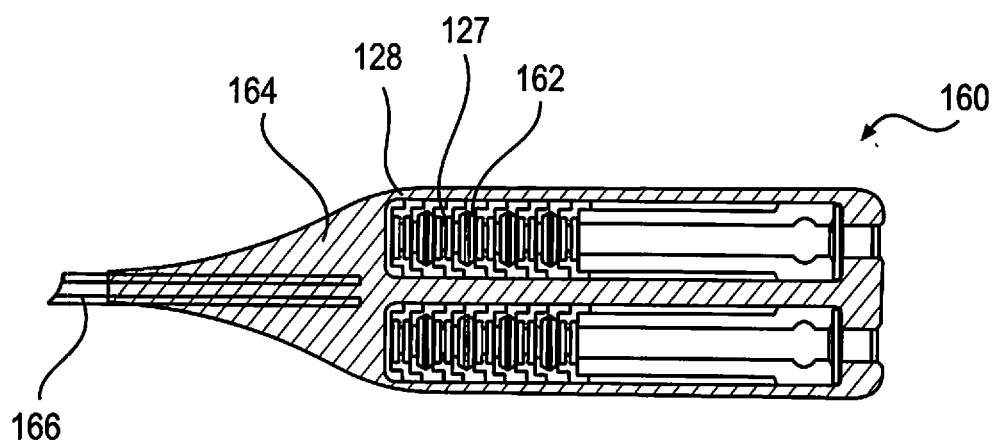
FIG. 11 depicts a lead splitter, according to an embodiment.

The lead splitter 160, as depicted in FIG. 11, is a fully implantable electrical medical accessory which is used in conjunction with the SCS 100 and typically a pair of 4-contact percutaneous leads 140. The primary function of the lead splitter 160 is to split a single lead 140 of eight contacts into a pair of 4 contact leads 140. The splitter 160 carries electrical signals from the IPG 102 to the proximal end of two 4-contact percutaneous stimulation leads 140. This allows the surgeon access to more stimulation areas by increasing the number of stimulation leads 140 available. The lead splitter 160 provides a robust, flexible, and bio-compatible electrical connection between the IPG 102 and proximal ends of the stimulation leads 140. The splitters 160 may be secured mechanically to the patient using either an anchor or a suture passed through tissue and tied around the body of the splitter 160. Splitters 160 are secured at the proximal end with a set-screw 119 on the IPG 102 which applies radial pressure to a fixation contact on the distal end of the proximal contacts of the splitter 160. The stimulation leads 140 are secured to the splitter 160 in a similar fashion, using a pair of set screws inside the molded tip of splitter 160 to apply a radial pressure to the fixation contact at the proximal end of each stimulation lead 140.

The lead splitter 160 consists of a combination of implantable materials. At the distal tip of the splitter 160 is a 2×4 array of implantable electrical contacts 162, with each contact 162 consisting of MP35 housing 128 and 90-10 platinum-iridium spring. A silicone seal 127 separates each of the housings 128. At the proximal end of each row of contacts 162 is a titanium (6Al4V) cap which acts as a stop for the lead, and at the distal tip, a titanium (6Al4V) block and set screw for lead fixation. The electrical contacts at the proximal end of the splitter 160 are made of a 90-10 platinum-iridium alloy utilized for its bio-compatibility and electrical conductivity. The polymeric body 164 of the lead 160 is polyurethane, chosen for its bio-compatibility, flexibility, and high lubricity to decrease friction while being passed through tissue. The polyurethane tubing 166 has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. Each lead splitter 160 has 8 proximal contacts (+1 fixation contact), and 2 rows of 4 contacts 162 at the distal end.

Anchors

Figure 12:
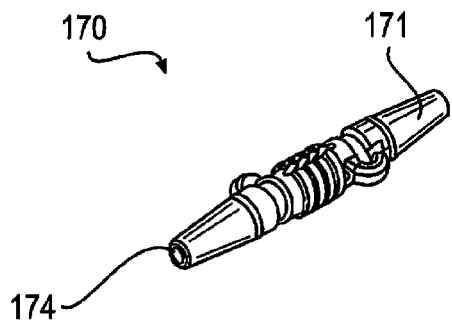
FIG. 12 depicts a sleeve anchor, according to an embodiment.
Figure 13:
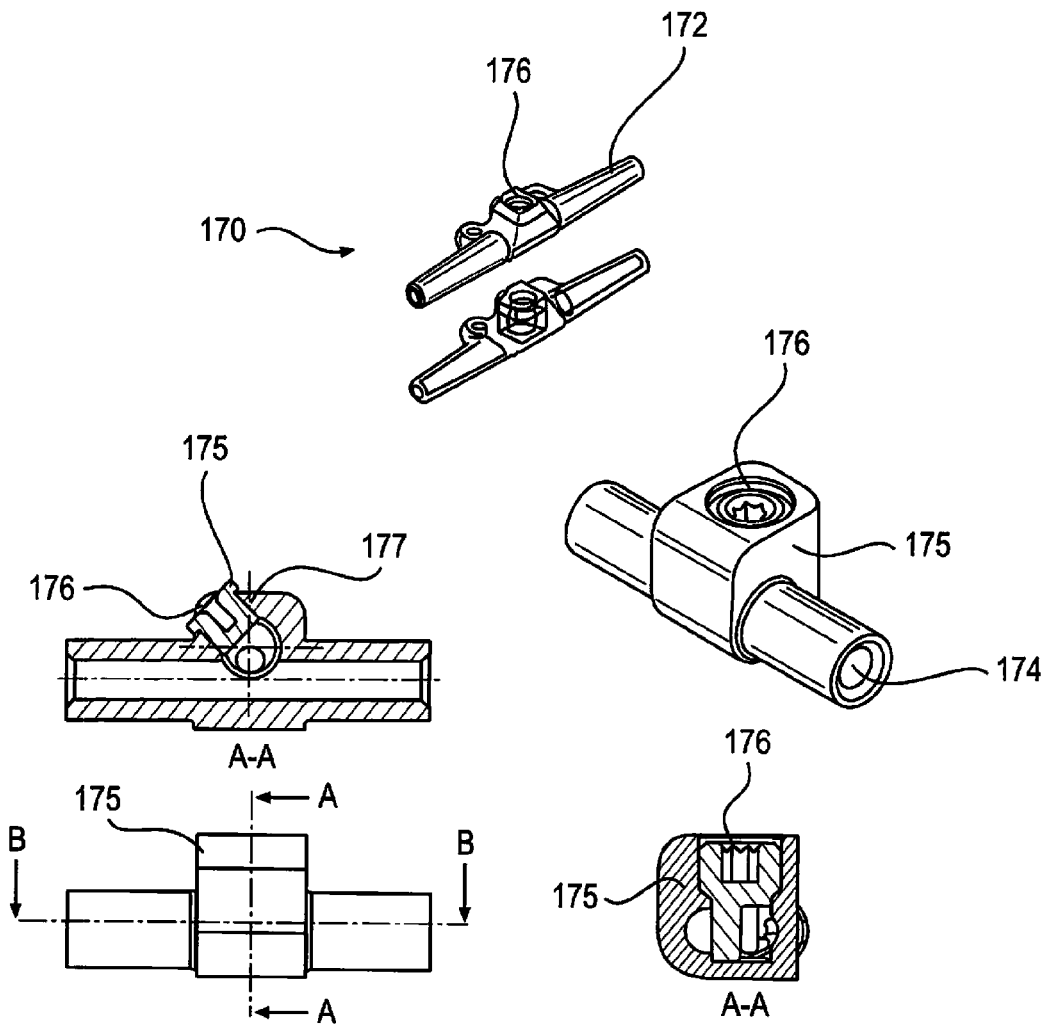
FIG. 13 depicts a mechanical locking anchor, according to an embodiment.

The lead anchor 170, as depicted in FIGS. 12 and 13, is a fully implantable electrical medical accessory which is used in conjunction with both percutaneous 140 and paddle 141 stimulation leads. The primary function of the lead anchor 170 is to prevent migration of the distal tip of the lead 140, 141 by mechanically locking the lead 140, 141 to the tissue. There are currently two types of anchors 170, a simple sleeve 171, depicted in FIG. 12, and a locking mechanism 172, depicted in FIG. 13, and each has a slightly different interface. For the simple sleeve type anchor 171, the lead 140, 141 is passed through the center thru-hole 174 of the anchor 171, and then a suture is passed around the outside of the anchor 171 and tightened to secure the lead 140, 141 within the anchor 171. The anchor 171 can then be sutured to the fascia. The locking anchor 172 uses a set screw 176 for locking purposes, and a bi-directional disposable torque wrench for locking and unlocking. Tactile and audible feedback is provided for both locking and unlocking.

Both anchors 171, 172 can be molded from implant-grade silicone, but the locking anchor 172 uses an internal titanium assembly for locking. The 3-part mechanism is made of a housing 175, a locking set screw 176, and a blocking set screw 177 to prevent the locking set screw from back out. All three components can be titanium (6Al4V). The bi-directional torque wrench can have a plastic body and stainless steel hex shaft.

Wireless Dongle

Figure 14:
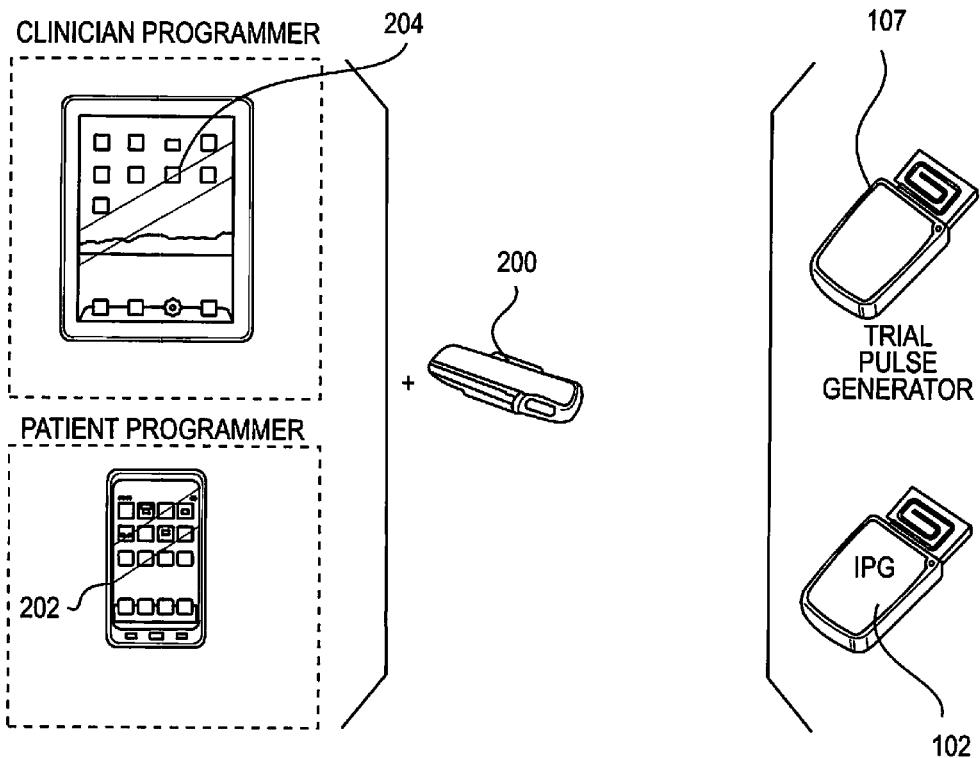
FIG. 14 illustrates communication via a wireless dongle with a tablet/clinician programmer and smartphone/mobile/patient programmer during trial and/or permanent implantation, according to an embodiment.

The wireless dongle 200 is the hardware connection to a smartphone/mobile 202 or tablet 204 that allows communication between the trial generator 107 or IPG 102 and the smartphone/mobile device 202 or tablet 204, as illustrated in FIG. 14. During the trial or permanent implant phases, the wireless dongle 200 is connected to the tablet 204 through the tablet 204 specific connection pins and the clinician programmer software on the tablet 204 is used to control the stimulation parameters. The commands from the clinician programmer software are transferred to the wireless dongle 200 which is then transferred from the wireless dongle 200 using RF signals to the trial generator 107 or the IPG 102. Once the parameters on the clinician programmers have been set, the parameters are saved on the tablet 204 and can be transferred to the patient programmer software on the smartphone/mobile device 202. The wireless dongle 200 is composed of an antenna, a microcontroller (having the same specifications as the IPG 102 and trial generator 107), and a pin connector to connect with the smartphone/mobile device 202 and the tablet 204.

Charger

The IPG 102 has a rechargeable lithium ion battery 108 to power its activities. An external induction type charger 210 (FIG. 1) wirelessly recharges the included battery 108 inside the IPG 102. The charger 210 is packaged into a housing and consists of a rechargeable battery, a primary coil of wire and a printed circuit board (PCB) containing the electronics. In operation, charger 210 produces a magnetic field and induces voltage into the coil 109 in the IPG 102. The induced voltage is then rectified and used to charge the battery 108 inside the IPG 102. To maximize the coupling between the coils, both internal and external coils are combined with capacitors to make them resonate at a particular common frequency. The coil acting as an inductor L forms an LC resonance tank. The charger uses a Class-E amplifier topology to produce the alternating current in the primary coil around the resonant frequency. The charger 210 features include, but are not limited to:

Charge IPG 102 wirelessly

Charge up to a maximum depth of 30 mm

Integrated alignment sensor indicates alignment between the charger and IPG 102 resulting in higher power transfer efficiency Alignment sensor provides audible and visual feedback to the user Compact and Portable A protected type of cylindrical Li ion battery is used as the charger 210 battery. A Class-E power amplifier topology is a much used type of amplifier for induction chargers, especially for implantable electronic medical devices. Due to the Class-E power amplifier's relatively high theoretical efficiency it is often used for devices where high efficiency power transfer is necessary. A 0.1 ohm high wattage resistor is used in series to sense the current through this circuit.

The primary coil L1 is made by 60 turns of Litz wire type 100/44-100 strands of 44 AWG each. The Litz wire solves the problem of skin effect and keeps its impedance low at high frequencies. Inductance of this coil was initially set at 181 uH, but backing it with a Ferrite plate increases the inductance to 229.7 uH. The attached ferrite plate focuses the produced magnetic field towards the direction of the implant. Such a setup helps the secondary coil receive more magnetic fields and aids it to induce higher power.

When the switch is ON, the resonance is at frequency $$f = \frac{1}{2\pi\sqrt{L1C2}}$$

When the switch is OFF, it shifts to $$f = \frac{1}{2\pi\sqrt{L1\frac{C1C2}{C1+C2}}}$$

In a continuous operation the resonance frequency will be in the range $$\frac{1}{2\pi\sqrt{L1C2}} < f < \frac{1}{2\pi\sqrt{L1\frac{C1C2}{C1+C2}}}$$

To make the ON and OFF resonance frequencies closer, a relatively larger value of C1 can be chosen by a simple criteria as follows C1=nC2; a value of n=4 was used in the example above; in most cases 3<n<10.

The voltages in these Class-E amplifiers typically go up to the order of 300 VAC. Capacitors selected must be able to withstand these high voltages, sustain high currents and still maintain low Effective Series Resistance (ESR). Higher ESRs result in unnecessary power losses in the form of heat.

The circuit is connected to the battery through an inductor which acts as a choke. The choke helps to smoothen the supply to the circuit. The N Channel MOSFET acts as a switch in this Class-E power amplifier. A FET with low ON resistance and with high drain current $I_d$ is desirable.

In summary, the circuit is able to recharge the IPG 102 battery 108 from 0 to 100% in approximately two hours forty-five minutes with distance between the coils being 29 mm. The primary coil and the Class-E amplifier draws DC current of 0.866 A to achieve this task. To improve the efficiency of the circuit, a feedback closed loop control is implemented to reduce the losses. The losses are minimum when the MOSFET is switched ON and when the voltage on its drain side is close to zero.

The controller takes the outputs from operational amplifiers, checks if the outputs meet the criteria, then triggers the driver to switch ON the MOSFET for the next cycle. The controller can use a delay timer, an OR gate and a 555 timer in monostable configuration to condition the signal for driver. When the device is switched ON, the circuit will not function right away as there is no active feedback loop. The feedback becomes active when the circuit starts to function. To provide an active feedback loop, an initial external trigger is applied to jump start the system.

Alignment Sensor

The efficiency of the power transfer between the external charger 210 and the internal IPG 102 will be maximum only when the charger 210 and IPG 102 are properly aligned. An alignment sensor is provided to ensure proper alignment as part of the external circuit design, and is based on the principle of reflected impedance. When the external coil is brought closer to the internal coil, the impedance of both circuits change. The sensing is based on measuring the reflected impedance and testing whether it crosses the threshold. A beeper provides an audible feedback to the patient and a LED provides visual feedback.

When the impedance of the circuit changes, the current passing through it also changes. A high power 0.1 ohm resistor can be used in the series of the circuit to monitor the change in current. The voltage drop across the resistor is amplified 40 times and then compared to a fixed threshold value using an operational amplifier voltage comparator. The output is fed to a timer chip which in turn activates the beeper and LED to provide feedback to the user.

The circuit can sense the alignment up to a distance of approximately 30 mm. The current fluctuation in the circuit depends on more factors than reflected impedance alone and the circuit is sensitive to other parameters of the circuit as well. To reduce the sensitivity related to other parameters, one option is to eliminate interference of all the other factors and improve the functionality of the reflected impedance sensor—which is very challenging to implement within the limited space available for circuitry. Another option is to use a dedicated sensor chip to measure the reflected impedance.

A second design uses sensors designed for proximity detector or metal detectors for alignment sensing. Chips designed to detect metal bodies by the effect of Eddy currents on the HF losses of a coil can be used for this application. The TDE0160 is an example of such a chip.

The external charger is designed to work at 75 to 80 kHz, whereas the proximity sensor was designed for 1 MHz. The sensor circuit is designed to be compatible with the rest of the external and is fine tuned to detect the internal IPG 102 from a distance of approximately 30 mm.

Programmer

The Clinician Programmer is an application that is installed on a tablet 204. It is used by the clinician to set the stimulation parameters on the trial generator 107 or IPG 102 during trial and permanent implantation in the operating room. The clinician programmer is capable of saving multiple settings for multiple patients and can be used to adjust the stimulation parameters outside of the operations room. It is capable of changing the stimulation parameters though the RF wireless dongle 200 when the trial generator 107 or IPG 102 which has been implanted in the patient is within the RF range. In addition, it is also capable of setting or changing the stimulation parameters on the trial generator 107 and/or the IPG 102 through the internet when both the tablet 204 and the Patient Programmers on a smartphone/mobile device 202 both have access to the internet.

The Patient Programmer is an application that is installed on a smartphone/mobile device 202. It is used by the patient to set the stimulation parameters on the trial generator 107 or IPG 102 after trial and permanent implantation outside the operating room. The clinician programmer is capable of saving multiple settings for multiple patients and can be transferred to the Patient Programmer wirelessly when the Clinician Programmer tablet 204 and the Patient Programmer smartphone/mobile device 202 are within wireless range such as Bluetooth from each other. In the scenario where the Clinician Programmer tablet 204 and the Patient Programmer smartphone/mobile device 202 are out of wireless range from each other, the data can be transferred through the internet where both devices 202, 204 have wireless access such as Wi-Fi. The Patient Programmer is capable of changing the stimulation parameters on the trial generator 107 or IPG 102 though the RF wireless dongle 200 when the trial generator 107 or IPG implanted in the patient is within the RF range.

Tuohy Needle

Figure 15:
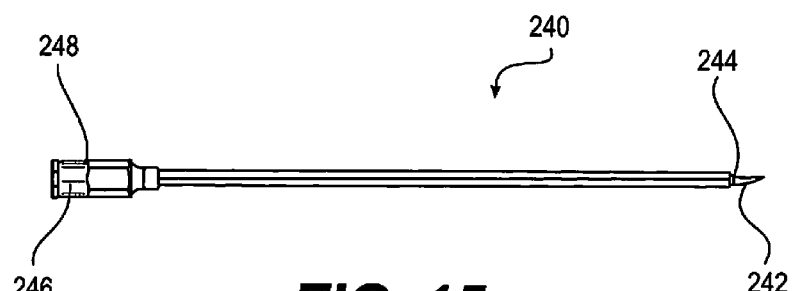
FIG. 15 depicts a Tuohy needle, according to an embodiment.

The Tuohy needle 240, as depicted in FIG. 15, is used in conjunction with a saline-loaded syringe for loss-of-resistance needle placement, and percutaneous stimulation leads 140, for lead 140 placement into the spinal canal. The Tuohy epidural needle 240 is inserted slowly into the spinal canal using a loss-of-resistance technique to gauge needle 240 depth. Once inserted to the appropriate depth, the percutaneous stimulation lead 140 is passed through the needle 240 and into the spinal canal.

The epidural needle 240 is a non-coring 14G stainless steel spinal needle 240 and will be available in lengths of 5" (127 mm) and 6" (152.4). The distal tip 242 of the needle 240 has a slight curve to direct the stimulation lead 140 into the spinal canal. The proximal end 246 is a standard Leur-Lock connection 248.

Stylet

Figure 16:
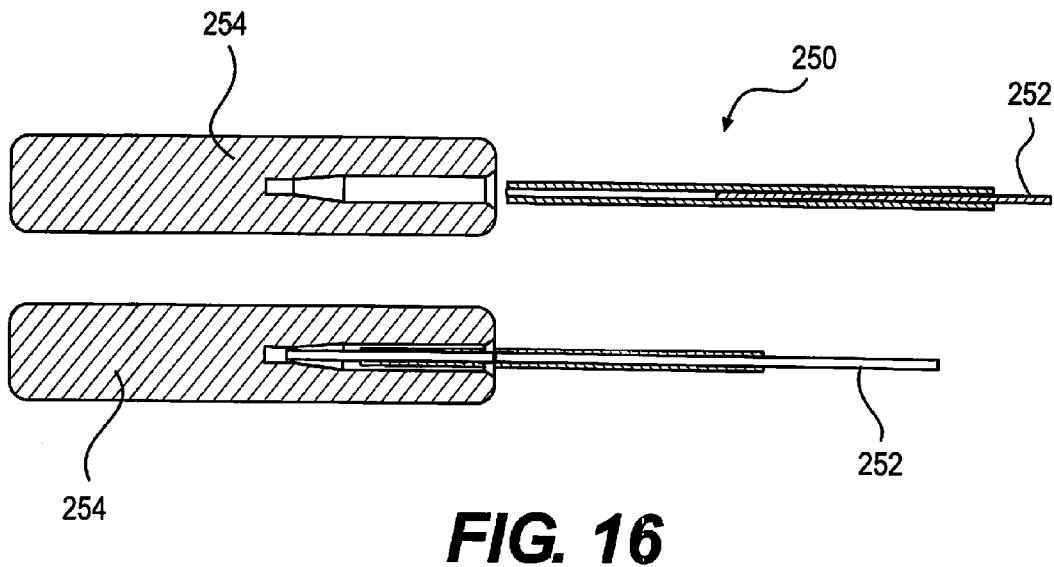
FIG. 16 depicts a stylet, according to an embodiment.

The stylet 250, as depicted in FIG. 16, is used to drive the tip of a percutaneous stimulation lead 140 to the desired stimulation zone by adding rigidity and steerability. The stylet 250 wire 252 passes through the center lumen 142 of the percutaneous lead 140 and stops at the blocking plug at the distal tip of the lead 140. The tip of the stylet 250 comes with both straight and curved tips. A small handle 254 is used at the proximal end of the stylet 250 to rotate the stylet 250 within the center lumen 142 to assist with driving. This handle 254 can be removed and reattached allowing anchors 170 to pass over the lead 140 while the stylet 250 is still in place. The stylet 250 wire 252 is a PTFE coated stainless steel wire and the handle 254 is plastic.

Passing Elevator

Figure 17:
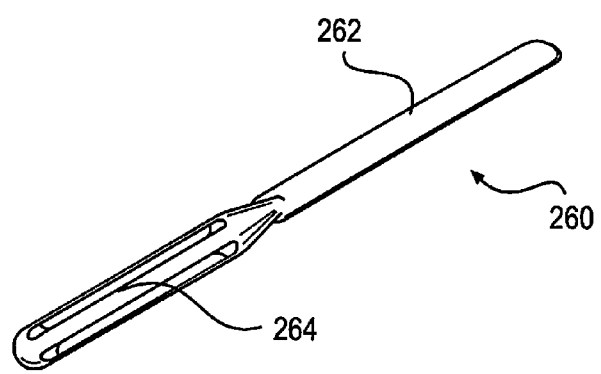
FIG. 17 depicts a passing elevator, according to an embodiment.

The passing elevator 260, as depicted in FIG. 17, is used prior to paddle lead 141 placement to clear out tissue in the spinal canal and help the surgeon size the lead to the anatomy. The passing elevator 260 provides a flexible paddle-shaped tip 262 to clear the spinal canal of obstructions. The flexible tip is attached to a surgical handle 264.

The passing elevator 260 is a one-piece disposable plastic instrument made of a flexible high strength material with high lubricity. The flexibility allows the instrument to easily conform to the angle of the spinal canal and the lubricity allows the instrument to easily pass through tissue.

Tunneling Tool

Figure 18:
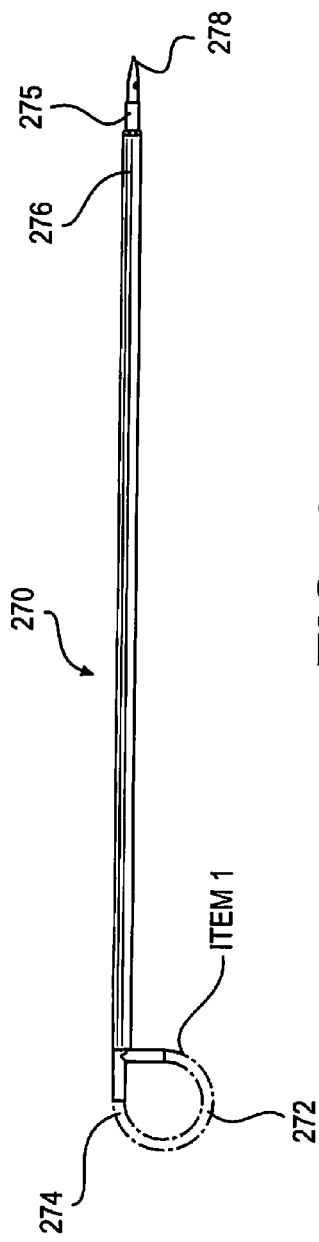
FIG. 18 depicts a tunneling tool, according to an embodiment.

The tunneling tool 270, as depicted in FIG. 18, is used to provide a subcutaneous canal to pass stimulation leads 140 from the entrance point into the spinal canal to the IPG implantation site. The tunneling tool 270 is a long skewer-shaped tool with a ringlet handle 272 at the proximal end 274. The tool 270 is covered by a plastic sheath 276 with a tapered tip 278 which allows the tool 270 to easily pass through tissue. Once the IPG 102 implantation zone is bridge to the lead 140 entrance point into the spinal canal, the inner core 275 is removed, leaving the sheath 276 behind. The leads 140 can then be passed through the sheath 276 to the IPG 102 implantation site. The tunneling tool 270 is often bent to assist in steering through the tissue.

The tunneling tool 270 is made of a 304 stainless steel core with a fluorinated ethylene propylene (FEP) sheath 276. The 304 stainless steel is used for its strength and ductility during bending, and the sheath 276 is used for its strength and lubricity.

Torque Wrench

Figure 19:
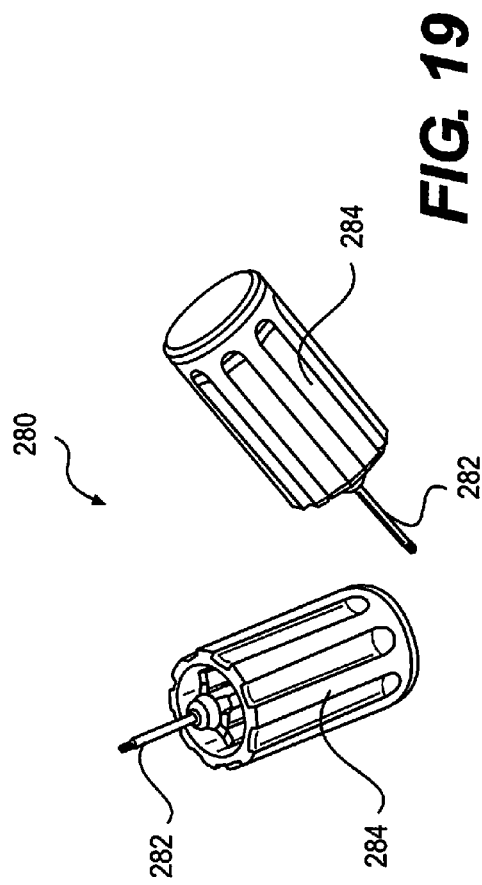
FIG. 19 depicts a torque wrench, according to an embodiment.

The torque wrench 280, as depicted in FIG. 19, is used in conjunction with the IPG 102, lead extension 150 and lead splitter 160 to tighten the internal set screw 119, which provides a radial force against the fixation contact of the stimulation leads 140, 141, preventing the leads 140, 141 from detaching. The torque wrench 280 is also used to lock and unlock the anchor 170. The torque wrench 280 is a small, disposable, medical instrument that is used in every SCS 100 case. The torque wrench 280 provides audible and tactile feedback to the surgeon that the lead 140, 141 is secured to the IPG 102, extension 150, or splitter 160, or that the anchor 170 is in the locked or unlocked position.

The torque wrench 280 is a 0.9 mm stainless steel hex shaft 282 assembled with a plastic body 284. The wrench's 280 torque rating is bi-directional, primarily to provide feedback that the anchor 170 is either locked or unlocked. The torque rating allows firm fixation of the set screws 119, 152 against the stimulation leads 140, 141 without over-tightening.

Trial Patch

The trial patch is used in conjunction with the trialing pulse generator 107 to provide a clean, ergonomic protective cover of the stimulation lead 140, 141 entrance point in the spinal canal. The patch is also intended to cover and contain the trial generator 107. The patch is a large, adhesive bandage that is applied to the patient post-operatively during the trialing stage. The patch completely covers the leads 140, 141 and generator 107, and fixates to the patient with anti-microbial adhesive.

The patch is a watertight, 150 mm×250 mm anti-microbial adhesive patch. The watertight patch allows patients to shower during the trialing period, and the anti-microbial adhesive decreases the risk of infection. The patch will be made of polyethylene, silicone, urethane, acrylate, and rayon.

Magnetic Switch

The magnetic switch is a magnet the size of a coin that, when placed near the IPG 102, can switch it on or off. The direction the magnet is facing the IPG 102 determines if the magnetic switch is switching the IPG 102 on or off.

Figure 20:
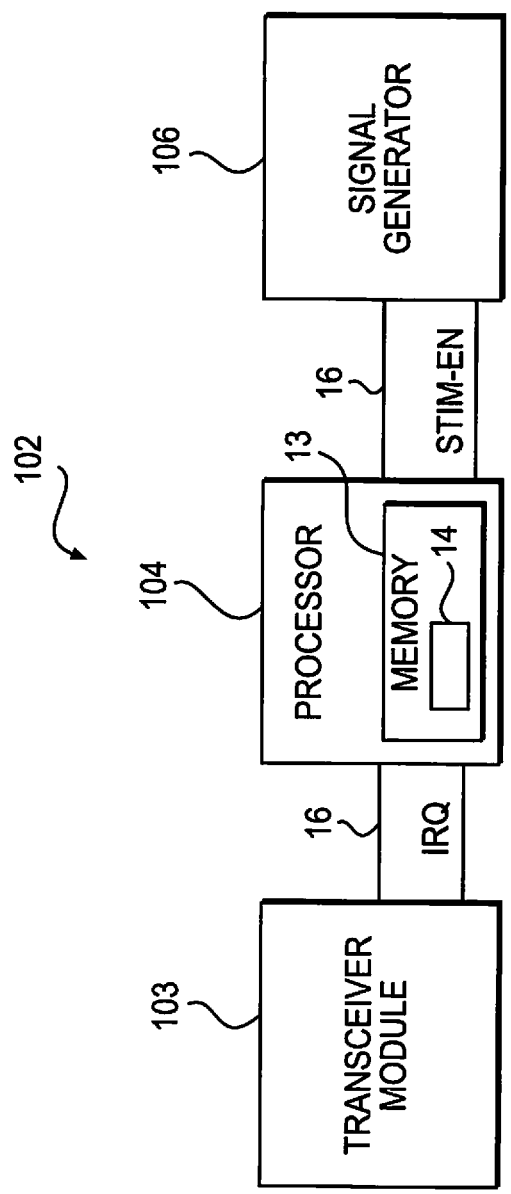
FIG. 20 is a function block diagram of some components in an implantable pulse generator according to an embodiment.

As shown in FIG. 20, the implantable pulse generator (IPG) 102 includes an RF transceiver module 103, a processor such as the microcontroller 104 and a programmable signal generator such as the ASIC 106. The transceiver module 103 manages wireless communication between the microcontroller 104 and external remote (e.g., dongle 200 connected to either the smartphone/mobile 202 or tablet 204).

In the embodiment shown in FIG. 20, a treatment control module 14 stored in a flash memory 13 of the microcontroller 104 is executed by the microcontroller to centrally control operation of every component and circuits of the IPG 102 with the exception of an independently operated charger (not shown) that charges the battery 108. Specifically, the treatment control module 14 handles programming of the RF transceiver module 103 and signal generator 106 among other functions. Communications among the microcontroller 104, RF transceiver module 103 and signal generator 106 are performed over a bus 16 such as the Serial Peripheral Interface (SPI) bus.

One exemplary microcontroller 104 may be MSP430F5328 from Texas Instruments of Dallas, Tex. as it has very low power usage, large amount of memory, integrated peripherals and small physical size.

Figure 21:
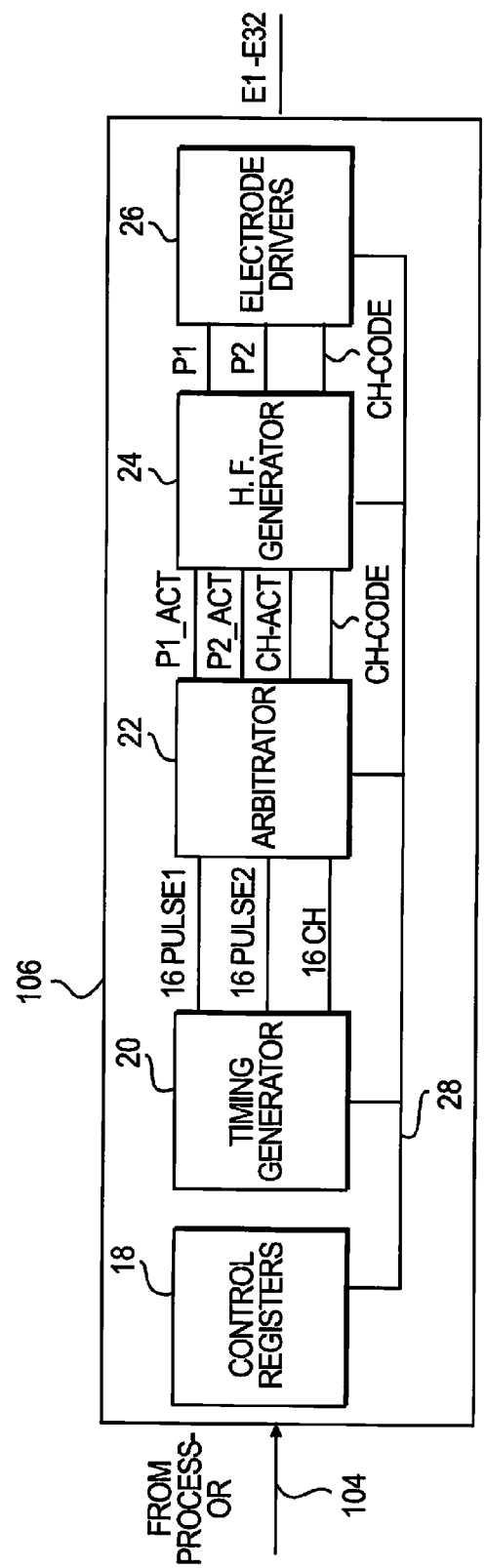
FIG. 21 is a functional block diagram of the signal generator of FIG. 20.

As shown in more detail in FIG. 21, the signal generator 106 includes memory (control registers 18), timing generator 20, arbitrator circuit 22, high frequency generator 24, electrode driver 26 which are all coupled to each other. All components in FIG. 21 have access to and are supplied with signal parameters stored in the control registers 18 through a register bus 28.

One of the many novel features of the IPG 102 is that the control registers 18 in the signal generator 106 have sufficient memory to store all of the signal parameters necessary to drive the electrodes E1-E32 independently of the microcontroller 104. As a result, the microcontroller 104 can be placed in a standby mode once it programs all of the pulse parameters in the control registers 18 and the treatment control module 14 instructs the signal generator to generate the stimulation signals by setting the stimulation enable pin STIM-EN to logic high. In the embodiment shown in which the microcontroller is MSP430F5328, the treatment control module 14 places the microcontroller in LPM3 Standby Mode. In an LPM3 mode, the master clock (main clock) that drives the instruction execution unit of the microcontroller 104 is turned off, essentially turning the microcontroller off so as to conserve battery power.

The microcontroller can be waken up from the standby mode by an interrupt signal IRQ which can be transmitted by the transceiver module 103 when it receives an appropriate instruction from a remote control device.

As discussed earlier, in the IPG 102, the electrodes E1-E32 may be grouped into stimulation sets (stimulation channels). Each stimulation channel represents one particular stimulation signal/pattern which is applied to the associated electrodes. In the embodiment shown, the IPG 102 can accommodate up to 16 channels (ch1 through ch16). Each electrode can belong to one or more channels up to the maximum number of channels and each channel can be associated with at least 2 electrodes to a maximum of 32 electrodes. Accordingly, one electrode can belong to all 16 channels.

Figure 25:
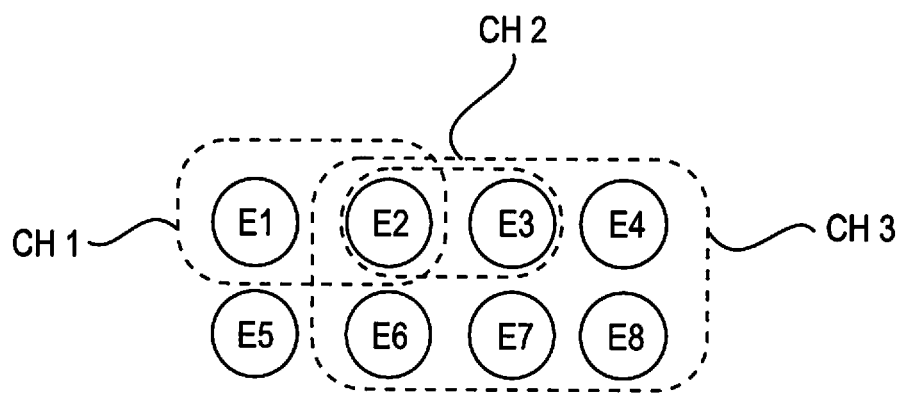
FIG. 25 illustrates a grouping of electrodes for different channels according to an embodiment of the present invention.

For example, as shown in FIG. 25, channel 1 includes electrodes E1 and E2, channel 2 includes electrodes E2 and E3 while channel 3 includes electrodes E2-E4 and E6-E8. Thus, electrode E2 belongs to channels 1, 2 and 3, electrode E3 belongs to channels 2 and 3, while electrode E4 and E5-E8 belong to only channel 3 and electrode E1 belong to only channel 1. In FIG. 25, electrode E5 is unused and therefore does not belong to any channel. Data that associates electrodes to particular stimulation channels are stored in the control registers 18.

Figure 26:
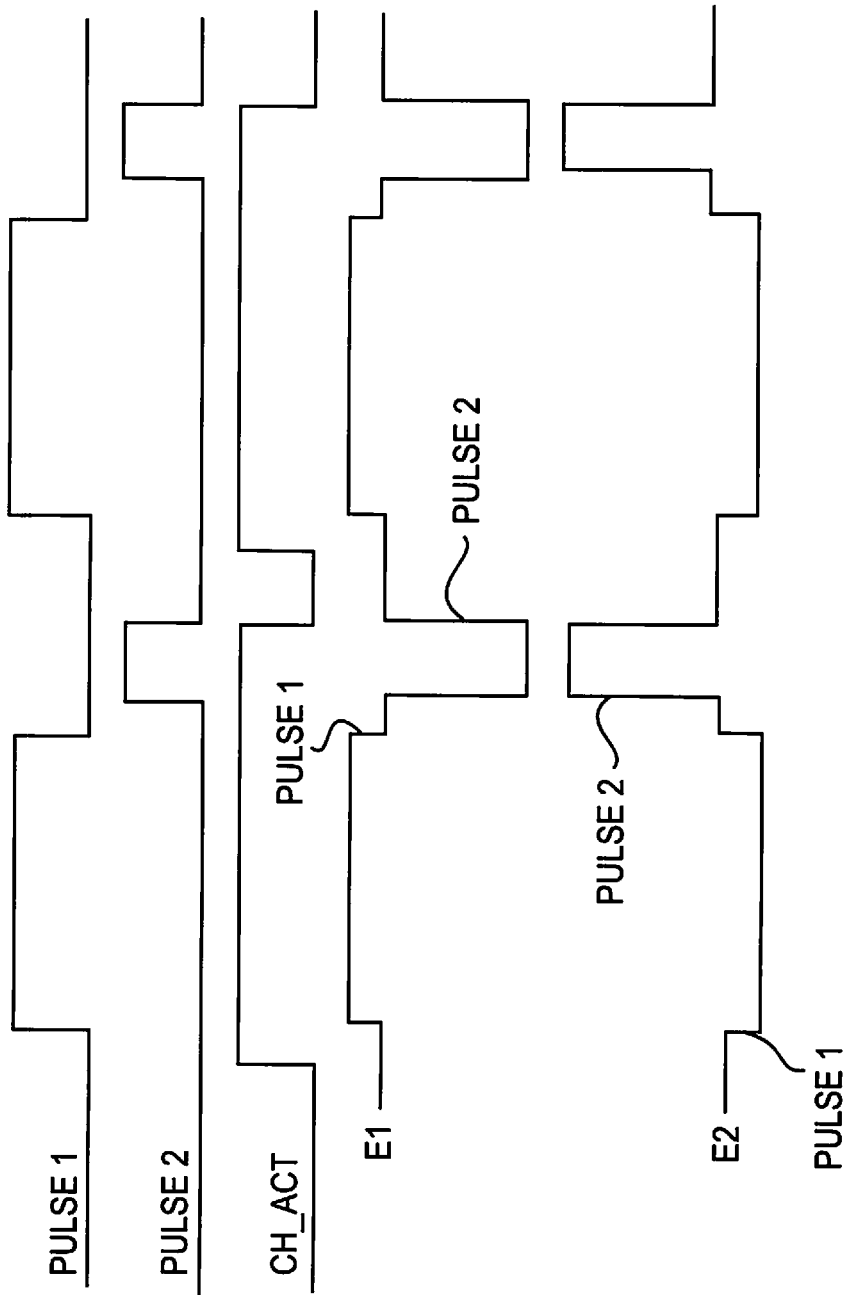
FIG. 26 shows exemplary electrode waveforms illustrating an asymmetrical pulse pattern between a positive and negative pulse according to an embodiment of the present invention.

As will be discussed more fully later herein, for each channel, the IPG 102 is capable of programming the amplitude, frequency and duration of both the first phase pulse (pulse1) and the second phase pulse (pulse2) of a biphasic pulse (see FIG. 26, for example) for all of the stimulation channels. As seen in FIG. 26, waveforms of a biphasic pulse comprising pulse1 and pulse2 of an active channel (ch_act) are combined into a single pulse pattern which are applied to the electrodes belonging to the active channel such as E1 and E2. FIG. 26 illustrates the pulse width and amplitude variations. As can be seen, the width of pulse1 is wider than that of pulse2 while the amplitude for pulse1 as scaled by the pulse scaler 38 (see positive pulse of E1, for example) is lower than that of pulse2 (see negative pulse of E1, for example).

The pulse parameters for pulse1 are independent of those for pulse2 for maximum flexibility in managing pain. As an example and referring to FIG. 25, assume that the current path between electrodes E1 and E2 (channel 1) affects a nerve path to a left leg while the current path between electrodes E2 and E3 (channel 2) affects a nerve path to a right leg. When the patient complains of more pain on the right leg than the left leg, a physician programming the IPG 102 may associate electrodes E1 and E2 to channel 1 with a stimulation pulse pattern having 100 Hz in frequency and associate electrodes E2 and E3 to channel 2 with a pulse pattern having 1000 Hz in frequency and a higher current amplitude than channel 1. In this way, smaller current is applied to channel 1 for the left leg and higher current is applied to channel 2 for the right leg. Advantageously, the flexibility of the IPG 102 allows just the right amount of current to each affected area of the patient.

The control registers 18 include standard read/write registers 18 that can be accessed by the SPI bus 16 and register bus 28. The control registers 18 are configured as an array of 8-bit registers, each with a unique address. The control registers 18 are programmed by the microcontroller 104 to store all pulse parameters that are necessary for the signal generator 106 to generate all of the stimulation channel patterns without any intervention from the microcontroller. The pulse parameters include stimulation channel timing settings, current (pulse amplitude) scaler settings, calibration data and electrode group parameters.

For each channel, the control registers 18 store the rising and falling edges of the channel itself, rising and falling edges of each of the two pulses (pulse1 and pulse2), period of the biphasic pulse, active channel period (channel envelope), and current scaling (pulse amplitude) values for both pulses (pulse1 and pulse2). For each channel, the control registers 18 also store burst frequency data (as will be explained later herein) such as burst period for both pulses (pulse1 and pulse2). For each channel, the control registers 18 also store data regarding which electrodes E1-E32 belong to that channel. For each channel and for each electrode within that channel, the control registers 18 store source/sink data for both pulses of the biphasic pulse (pulse1 and pulse2), i.e., whether each electrode will be sourcing current or sinking current during pulse1 and pulse2. All parameters are specified with reference to the origin and is in units of microseconds.

The timing generator 20 generates stimulation timing signals which comprise pulse1, pulse2, and a channel pulse "ch" (channel envelope waveform) for all 16 channels based on the pulse timing parameters stored in the control registers 18. If all 16 channels are programmed by the clinician, then the timing generator 20 generates the pulse1, pulse2, and channel pulse data ch for all 16 channels simultaneously.

As an example, pulse1 and pulse2 waveforms of FIG. 26 illustrate the output waveforms from the timing generator 20 for an exemplary biphasic pulse of a particular channel. The channel envelope data ch_act defines the start and end of an active portion of each channel as well as the channel period, which can be defined as the time between two adjacent rising edges of the channel. Pulse1 and Pulse2 define the start and end of each of the two phases of the biphasic pulse.

Because of the flexibility of the IPG 102, more than one channel could become active at any time when stimulation patterns of multiple channels are programmed. The arbitrator 22 is designed to resolve the overlapping channel (channel contention) problem by ensuring that only one channel is active at any one time. Among others, the circuits in the arbitrator 22 are designed with two rules. The first rule is that when an active channel is being selected (i.e., a channel currently in progress), all other channels attempting to go active are suppressed and discarded. The second rule is that when two or more channels are about to become active with simultaneous rising edges in ch, an active channel will be determined based on a predetermined channel priority.

In the embodiment shown, the arbitrator 22 has been programmed such that the lowest numbered channel will be given priority and the remaining simultaneous channels will be discarded. Since there are 16 channels (ch1 through ch16) in the IPG 102, channel one has the highest priority while channel 16 has the lowest priority.

The output of the arbitrator 22 includes pulse timing signal p1_act and p2_act which are the same waveforms as pulse1 and pulse2 of an active channel. The arbitrator 22 also outputs the channel envelope of an active channel (ch_act as shown in FIG. 26, for example) for use by the high frequency generator 24 as well as the channel number of the active channel (ch_code), which will be used by the electrode driver 26, as will be explained later herein. In the embodiment shown, the channel number is a 4-bit code that identifies the number of the active channel. For example, '0001' represents channel 2 while '1111' represents channel 16.

Figure 27:
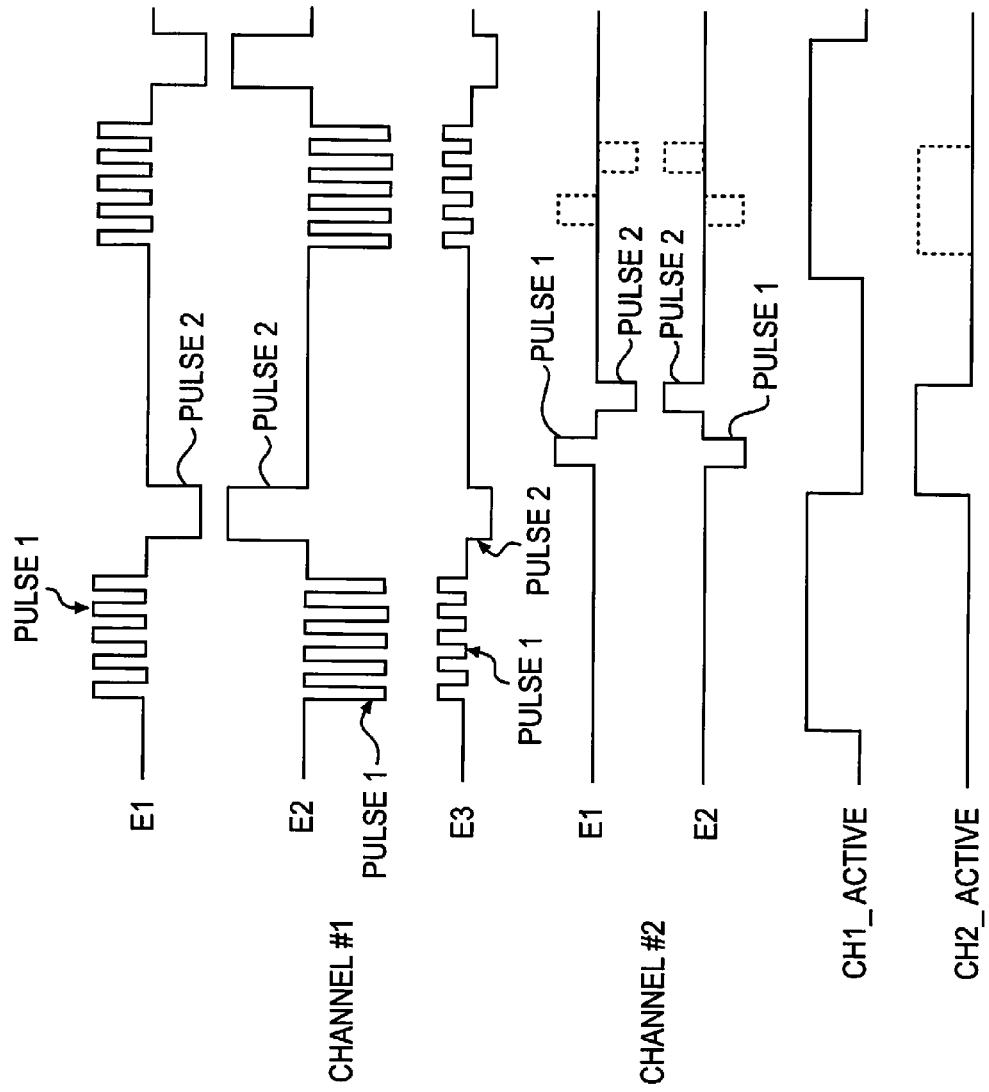
FIG. 27 shows exemplary electrode waveforms for two arbitrated stimulation channels according to an embodiment of the present invention.

FIG. 27 provides an example of the channel arbitration by the arbitrator 22. In FIG. 27, channel number one has 3 electrodes E1-E3 and channel number two has 2 electrodes E1-E2. As the channel period for the two channels is different, they will overlap from time to time. In the illustration, channel one is active (ch1_active) when channel two attempts to become active. At that time, the arbitrator executes the first rule, and will suppress channel two and prevent it from becoming active. Thus, only the pulse1/pulse2 signals that drive the electrodes for channel one (active channel) will be output by the arbitrator 22. The pulse1/pulse2 signals and channel envelope signal for channel two (ch2_active) are shown in dotted lines to show that they have been suppressed by the arbitrator 22.

The high frequency generator 24 receives the p1_act and p2_act waveforms from the arbitrator 22, decides whether to modulate the received signals based on the stored parameters in the control registers 18. If the decision is no, then the high frequency generator 24 passes the received pulse signals unaltered to the electrode driver 26.

If the decision is a yes, however, the high frequency generator 24 modulates the received signals at a burst frequency that has been programmed into the control registers 18. The burst frequency is higher than the frequency of the received signals p1_act and p2_act.

The electrode driver 26 receives the output (p1, p2 and ch_code) of the high frequency generator 24, amplifies the received signal according to the pulse amplitude parameters stored in the control registers 18, and outputs the final stimulation pattern for each channel to be applied through the electrodes E1-E32. As discussed above, the burst pulse parameters stored in the control registers 18 have separate frequency values for pulse1 and pulse2 such that an asymmetric pulse shape with positive and negative pulses having different frequency values can be generated by the electrode driver 26.

Figure 22:
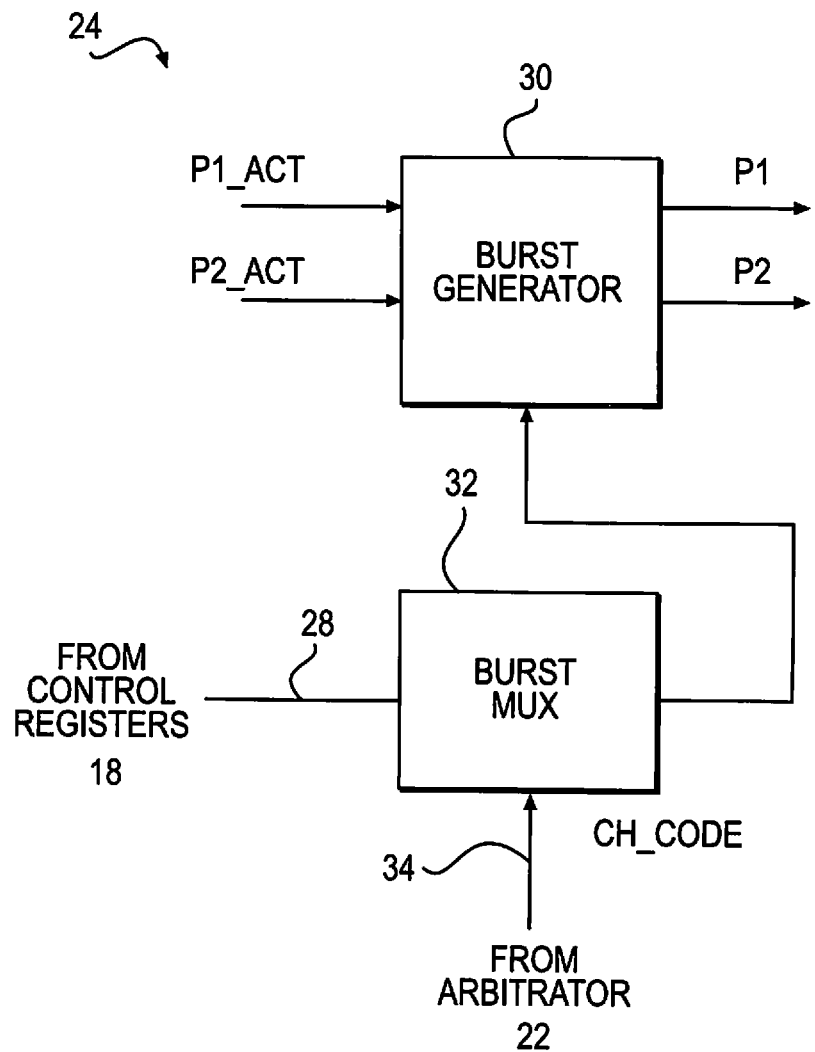
FIG. 22 is a functional block diagram of the high frequency generator of FIG. 21.

FIG. 22 is a more detailed functional block diagram of the high frequency generator of FIG. 21. The high frequency generator 24 includes a burst generator 30 and burst multiplexer 32.

The burst multiplexer 32 receives burst parameters stored in the control registers 18 for all the channels, selects the burst parameters associated with an active channel, and outputs the selected burst parameters to the burst generator 30. Specifically, there is a pulse1/pulse2 burst register pair for each channel for the burst option, totaling 32 registers for the 16 possible channels in the embodiment shown. The burst multiplexer 32 is a vector MUX that selects the pulse1/pulse2 register pair corresponding to the active channel number. The select lines 34 to the burst multiplexer 32 is the active channel number (ch_code) from the arbitrator 22, which identifies the active channel at any given time. The selected burst parameters for pulse1/pulse2 are sent to the burst generator 30.

Within the burst generator 30, there are 2 independent burst generator circuits, one for pulse1 and one for pulse2. The pulse1 and pulse2 signals belonging to the active channel are passed through to the burst generator circuits from the arbitrator 22. If the pulse1/pulse2 burst parameter data stored in the control registers 18 is zero (therefore the selected burst parameters to the burst generator 30 are also zero), then no burst is generated, in which case the pulse1/pulse2 signals from the arbitrator 22 are sent unaltered to the electrode driver 26. If the pulse1/pulse2 burst register in the control registers 18 is programmed, then the pulse1/pulse2 duration will be replaced by (modulated to) the corresponding programmed burst signal based on the selected burst parameters from the burst multiplexer 32.

As an example, FIG. 27 illustrates that pulse1 for channel one has been programmed for high frequency modulation while pulse2 for the same channel has not been programmed. Specifically, a single pulse1 pulse has been modulated to (replaced with) five higher frequency burst pulses. Thus, the frequency of the newly modulated pulse1 is five times the frequency of the original pulse1 signal.

Figure 23:
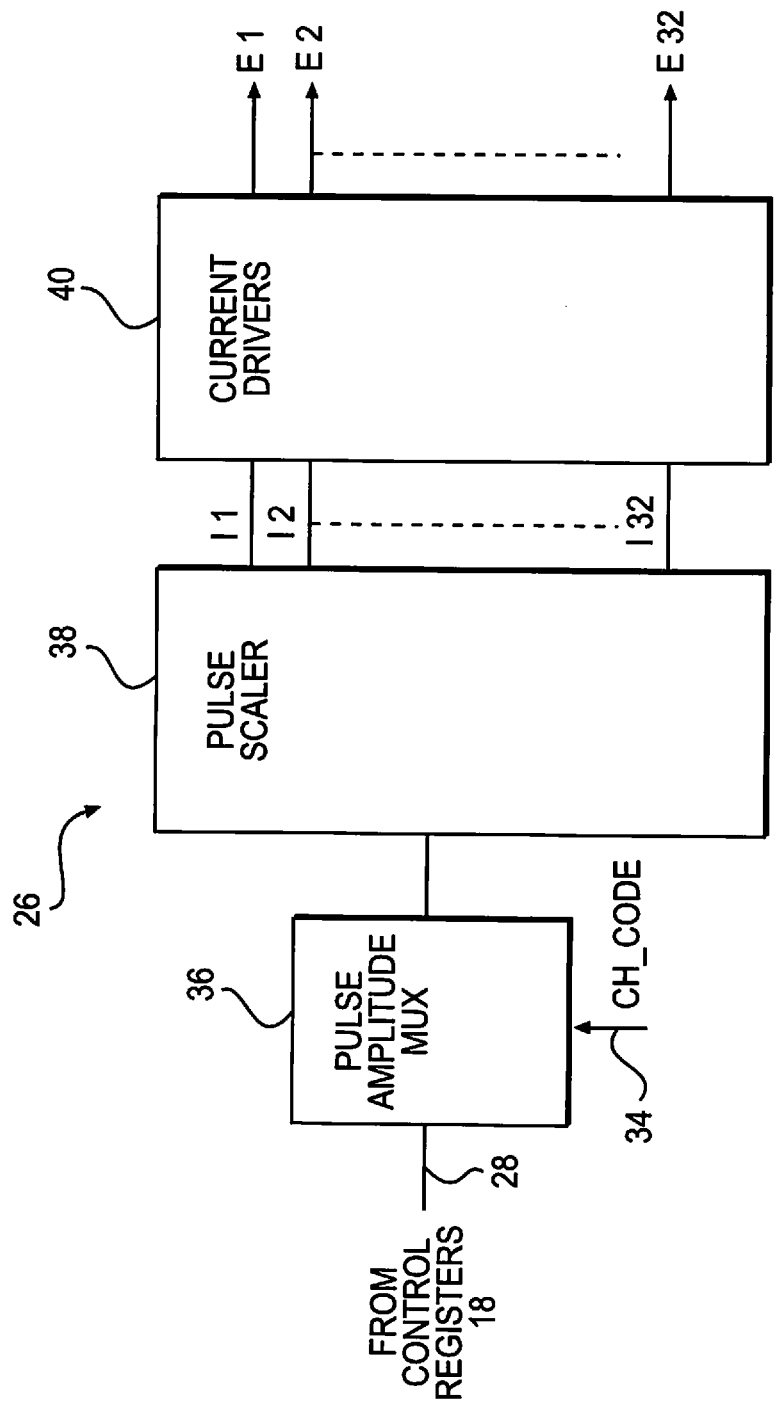
FIG. 23 is a functional block diagram of the electrode driver of FIG. 21.

FIG. 23 is a more detailed functional block diagram of the electrode driver 26 of FIG. 21. The electrode driver 26 includes a pulse amplitude multiplexer 36, pulse scaler 38 and current drivers 40.

The pulse amplitude multiplexer 36 receives amplitude parameters stored in the control registers 18 for all the channels, selects the amplitude parameters associated with an active channel, and outputs the selected amplitude parameters to the pulse scaler 38.

Specifically, 512 bytes (16 by 32 bytes—32 bytes for each channel) in the control registers 18 are reserved for storing pulse amplitude data. Each of the 16 channels is associated with 32 bytes with each byte representing pulse amplitude information for pulse1 and pulse2 of each of the 32 electrodes E1-E32. From one byte, 7 bits are used to store the amplitude information for pulse1 and pulse2 and the remaining bit (MSB) defines the polarity of the pulse at the associated electrode as will be discussed later herein.

Similar to the burst multiplexer 32, the pulse amplitude multiplexer 36 is a vector MUX that selects the 32 bytes of amplitude parameters for pulse1/pulse2 corresponding to the active channel number. The select lines 34 to the amplitude multiplexer 36 is the active channel number (ch_code) from the arbitrator 22, which identifies the active channel at any given time. The selected amplitude parameters of pulse1/pulse2 for all 32 electrodes E1-E32 are sent to the pulse scaler 38. The pulse scaler 38 outputs amplitude scaling factors for all electrodes of the active channel. Thus, the pulse scaler 38 includes 32 identical scalers corresponding to the 32 electrodes E1-E32. In the embodiment shown, each scaler includes a D/A converter that converts the digital amplitude value into a corresponding analog value I1-I32.

As discussed above, the signal generator 106 supports asymmetrical pulse amplitude feature, which means the amplitude for pulse1 and pulse2 can be different. The amplitude scaling data are stored in the control registers 18. In the embodiment shown, 4 bits are used to specify the scaling factor for pulse1 and pulse2 for each electrode—2 bits for pulse1 and 2 bits for pulse2. Moreover, the signal generator 106 can support asymmetrical pulse width variation between pulse1 and pulse2.

The pulse scaler 38 adjusts the amplitude parameter by the associated scaling factor stored in the associated 2 bits for pulse1 and pulse2. In the embodiment shown, the pulse scaler 38 performs the scaling function by shifting to the right the content of the selected amplitude parameter (7 bits of data from the amplitude multiplexer 36) by the number stored in the corresponding 2 bit scaling factor. Since there are four possibilities in a 2 bit number (0, 1, 2, or 3), the amplitude can be reduced by ½, ¼ or ⅛.

For example, assume that the active channel is channel one, the amplitude parameter for electrode E1 for channel one in the control registers 18 is binary "1111111" (decimal 127) while the associated 2 bit scaling factor is binary "11" for pulse1 and "01" for pulse2. The number 127 represents 12.7 mA of current. For pulse1, the 7 bit amplitude content will be shifted to the right by 3 bits (binary "11") for pulse1 and by 1 bit (binary "01") for pulse2. Thus, the pulse scaler 38 will scale the amplitude of 127 down to 15 (binary "1111") for pulse1 and to 63 (binary "111111") for pulse2, which corresponds to a current of 1.5 mA for pulse1 and 6.3 mA for pulse2.

In the embodiment shown, the scaling factor parameters are stored in unused bits of burst parameters and are passed to the pulse scaler 38 from the burst multiplexer 32. However, dedicated memory can be allocated in the control registers 18. It is to be noted that the stimulation programming software should ensure that at any given instant of time, the algebraic sum of all electrode currents is zero, and the dc average of the current per cycle at each electrode is also zero.

Another function performed by the pulse scaler 38 is that it converts the scaled amplitude digital value into an analog output current that is linearly proportional to the value of the digital value. The analog output current for each electrode is supplied to the current drivers 40. In the embodiment shown, the analog output current represents 1/20 of the actual current to be supplied to the associated electrode.

The current drivers 40 amplify the analog output currents from the pulse scaler 38 and switches the amplified current to the appropriate electrodes E1-E32 based on the pulse parameters stored in the control registers 18. Since there are 32 electrodes, there are 32 electrode drivers 40 in the embodiment shown. In the embodiment shown, each current driver 40 is a current driver that amplifies the input signal from the pulse scaler 38 by 20 times.

Figure 24:
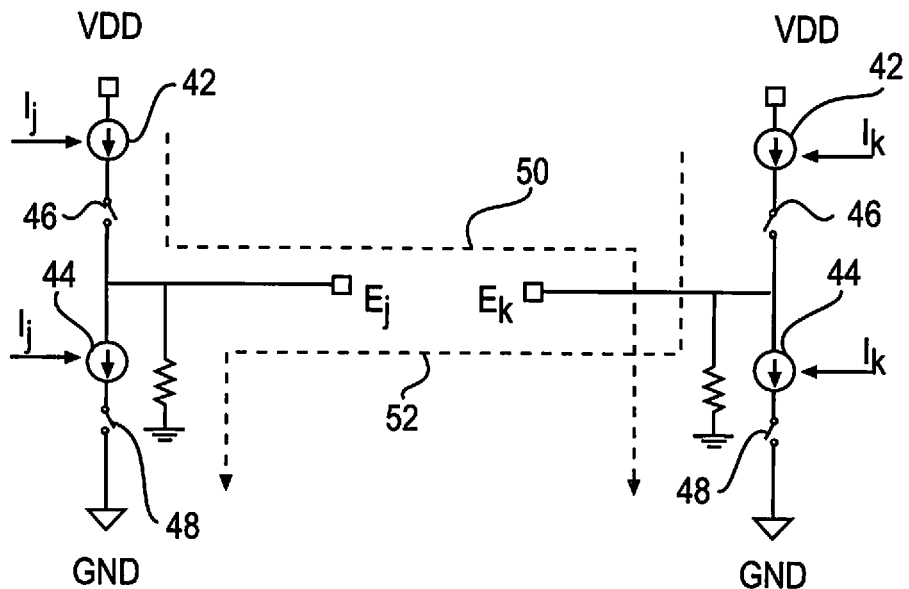
FIG. 24 is a functional illustration of two of the current drivers of FIG. 23.

FIG. 24 is a functional illustration of two of the current drivers of FIG. 23. Each electrode driver 40 can be a current source that can sink or source current whose amplitude is based on a control current signal coming from the pulse scaler 38. In the embodiment shown, the current source includes a pair of NMOS current source 42 and PMOS current source 44 that are coupled in series between the voltage supply and ground. Each of the PMOS and NMOS current sources can be implemented as a current mirror in a well-known manner. The NMOS current source 44 sinks current from the associated electrode to ground while the PMOS current source 44 sources current from the positive voltage supply to the associated electrode. Each electrode driver 40 includes switches 46 and 48 connected in series between the voltage supply and ground to either source or sink the current.

The control registers 18 store the pulse parameter that relate to whether a particular electrode will be sourcing current or sinking current. In the embodiment shown, bit 7 (MSB) of each byte of the pulse amplitude parameters that are supplied to the burst multiplexer 32 is used to specify whether a particular current source 40 will be sourcing current or sinking current. If the bit is zero, during pulse1, switch 46 will be turned on while switch 48 will be turned off, and during pulse2, switch 46 will be turned off while switch 48 will be turned on. If the bit is set (i.e., it is a "1"), during pulse1, switch 46 will be turned off while switch 48 will be turned on, and during pulse2, switch 46 will be turned on while switch 48 will be turned off.

FIG. 24 illustrates the current path for two electrodes Ej and Ek when bit 7 for Ej=0 and bit 7 for Ek=1. During pulse1, switch 46 for Ej and switch 48 for Ek turn on to create a current path 50. In that instance, the PMOS current source 42 for Ej will be sourcing current while the NMOS current source 44 for Ek will be sinking current to ground. Conversely, during pulse2, switch 46 for Ek and switch 48 for Ej turn on to create a current path 52. In that instance, the PMOS current source 42 for Ek will be sourcing current while the NMOS current source 44 for Ej will be sinking current to ground.

The pulse shape at the electrode Ej will look similar to the E1 waveform as shown in FIG. 26 while the pulse shape at the electrode Ek will look similar to the E2 waveform.

The foregoing specific embodiments represent just some of the ways of practicing the present invention. Many other embodiments are possible within the spirit of the invention. Accordingly, the scope of the invention is not limited to the foregoing specification, but instead is given by the appended claims along with their full range of equivalents.

What is claimed is:

1. An implantable pulse generator (IPG) that generates spinal cord stimulation signals for a human body, comprising:
    a signal generator for generating stimulation signals, said signal generator comprising:
        control registers storing stimulation signal parameters for a plurality of channels with each channel capable of being associated with at least two electrodes among a plurality of electrodes, each channel representing a stimulation signal pattern of the associated electrodes, the signal parameters including burst parameters that specify a frequency of the stimulation signal for each channel;
        a timing generator adapted to generate timing signals representing stimulation signals for the plurality of channels according to the stored signal parameters;
        a high frequency generator adapted to determine whether to modulate the timing signals received from the timing generator and modulate the received timing signals at a burst frequency according to the stored burst parameters so as to enable independent frequency control of the stimulation signals for each channel;
        an arbitrator; and
        an electrode driver for each electrode,
        wherein a registration bus electronically connects each of the control registers, the timing generator, the high frequency generator, the arbitrator, and the electrode driver for each electrode;
    a treatment control module configured to instruct the signal generator to generate the stimulation signals while a microcontroller electrically connected to the signal generator is in standby mode.

2. The IPG of claim 1, wherein the electrode driver for each of the plurality of electrodes is adapted to adjust the amplitude of the timing signals from the timing generator according to the stored signal parameters so as to enable independent amplitude control of the stimulation signals for each channel.

3. The IPG of claim 1, wherein when the high frequency generator has determined not to modulate the received timing signals, the high frequency generator outputs the received timing signals whose frequency is unaltered.

4. The IPG of claim 1, wherein the high frequency generator includes a burst multiplexer that:
    receives the burst parameters stored in the control registers;
    selects the burst parameters associated with an active channel; and
    outputs the selected burst parameters.

5. The IPG of claim 4, wherein the high frequency generator includes a burst generator that receives the selected burst parameters from the burst multiplexer and modulates the received timing signals according to the received burst parameters.

6. The IPG of claim 1, further comprising a transceiver module adapted to wirelessly communicate with a remote control and to transmit an interrupt signal to the microcontroller to wake up the microcontroller from the standby mode.

7. The IPG of claim 1, wherein the arbitrator continuously receives the generated timing signals and selects one channel among the plurality of channels as an active treatment channel.

8. The IPG of claim 7, wherein when the one channel is being selected as the active treatment channel, the arbitrator is adapted to suppress all other channels.

9. The IPG of claim 7, wherein when the generated timing signals indicate that two or more channels are about to become active at the same time when no active channel has been selected, the arbitrator is adapted to select the one channel as the active treatment channel based on a predetermined priority of the two or more channels.

* * * * *